(12) United States Patent
Banet et al.

(10) Patent No.: US 9,211,073 B2
(45) Date of Patent: Dec. 15, 2015

(54) NECKLACE-SHAPED PHYSIOLOGICAL MONITOR

(71) Applicant: Perminova Inc.

(72) Inventors: Matthew Banet, San Diego, CA (US); Susan Meeks Pede, Encinitas, CA (US); Marshal Singh Dhillon, San Diego, CA (US); Andrew Terry, San Diego, CA (US); Kenneth Robert Hunt, Vista, CA (US)

(73) Assignee: TOSENSE, INC., La Jolla, CA (US)

( * ) Notice: Subject to any disclaimer, the term of this patent is extended or adjusted under 35 U.S.C. 154(b) by 0 days.

(21) Appl. No.: 14/184,603

(22) Filed: Feb. 19, 2014

(65) Prior Publication Data

US 2014/0236031 A1  Aug. 21, 2014

Related U.S. Application Data

(60) Provisional application No. 61/767,180, filed on Feb. 20, 2013.

(51) Int. Cl.
*A61B 5/04* (2006.01)
*A61B 5/029* (2006.01)
*A61B 5/00* (2006.01)
(Continued)

(52) U.S. Cl.
CPC .............. *A61B 5/029* (2013.01); *A61B 5/6822* (2013.01); *A61B 5/6831* (2013.01); *A61B 5/0245* (2013.01); *A61B 5/02055* (2013.01);
(Continued)

(58) Field of Classification Search
CPC .............. A61B 5/029; A61B 5/02055; A61B 5/02116; A61B 5/02125; A61B 5/0245; A61B 5/0816; A61B 5/02438; A61B 5/6831; A61B 5/6813; A61B 5/683; A61B 5/6822; A61B 5/6823
See application file for complete search history.

(56) References Cited

U.S. PATENT DOCUMENTS 4,635,646 A * 1/1987 Gilles et al. ............. 600/509
4,662,378 A * 5/1987 Thomis ................. 600/382
(Continued)

OTHER PUBLICATIONS

Bernstein, Impedance cardiography: Pulsatile blood flow and the biophysical and electrodynamic basis for the stroke volume equations. J Electr Bioimp; 2010;1:2-17.
(Continued)

*Primary Examiner* — Michael Kahelin
*Assistant Examiner* — Mallika D Fairchild
(74) *Attorney, Agent, or Firm* — Michael A. Whittaker

(57) ABSTRACT

The invention provides a neck-worn sensor (referred to herein as the 'necklace') that is a single, body-worn system that measures the following parameters from an ambulatory patient: heart rate, pulse rate, pulse oximetry, respiratory rate, temperature, thoracic fluid levels, stroke volume, cardiac output, and a parameter sensitive to blood pressure called pulse transit time. From stroke volume, a first algorithm employing a linear model can estimate the patient's pulse pressure. And from pulse pressure and pulse transit time, a second algorithm, also employing a linear algorithm, can estimate systolic blood pressure and diastolic blood pressure. Thus, the necklace can measure all five vital signs along with hemodynamic parameters. It also includes a motion-detecting accelerometer, from which it can determine motion-related parameters such as posture, degree of motion, activity level, respiratory-induced heaving of the chest, and falls.

22 Claims, 15 Drawing Sheets

(51) Int. Cl.
  *A61B 5/0205* (2006.01)
  *A61B 5/021* (2006.01)
  *A61B 5/024* (2006.01)
  *A61B 5/0245* (2006.01)
  *A61B 5/08* (2006.01)

(52) U.S. Cl.
  CPC ........ *A61B 5/02116* (2013.01); *A61B 5/02125* (2013.01); *A61B 5/02438* (2013.01); *A61B 5/0816* (2013.01)

(56) References Cited

U.S. PATENT DOCUMENTS

2007/0106167 A1* 5/2007 Kinast ........................ 600/509
2008/0287768 A1* 11/2008 Kuo et al. .................... 600/382

OTHER PUBLICATIONS

Fuller, The validity of cardiac output measurement by thoracic impedance: A meta-analysis. Clin Invest Med. Apr. 1992;15(2):103-112.

* cited by examiner

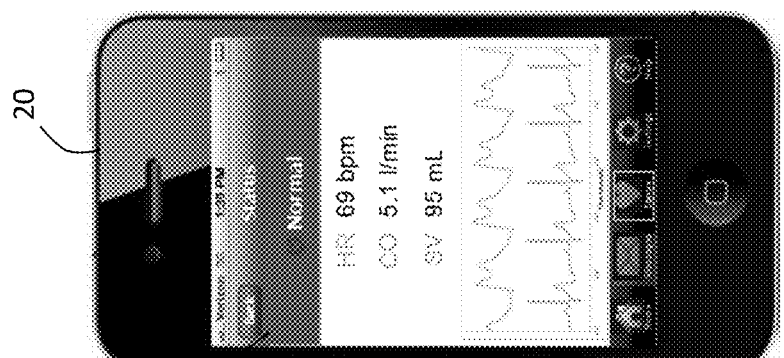
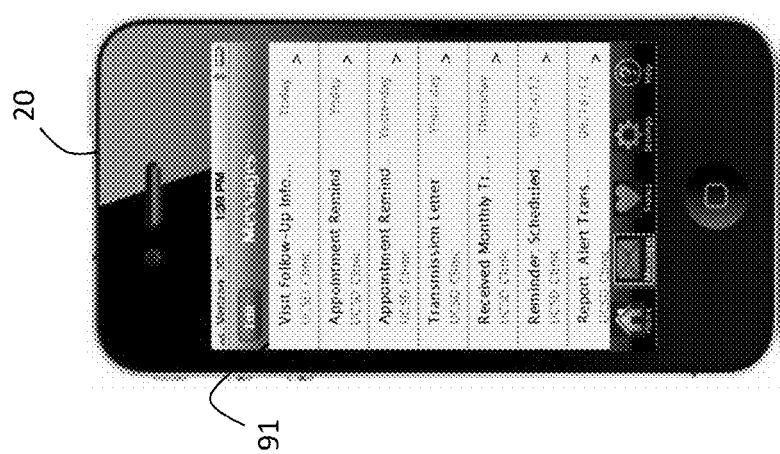
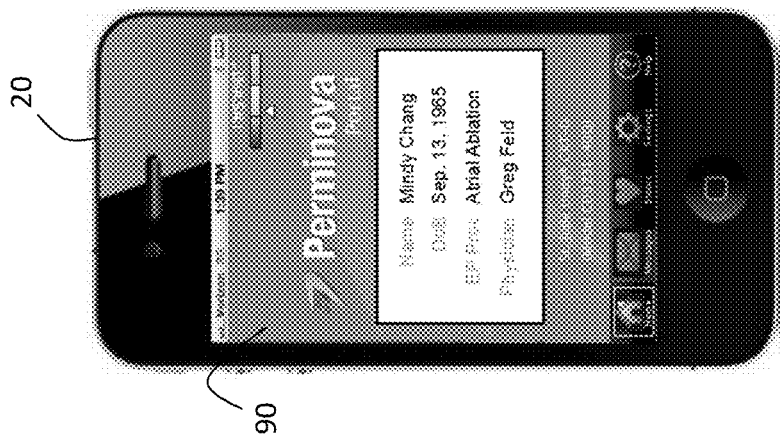
FIG. 13

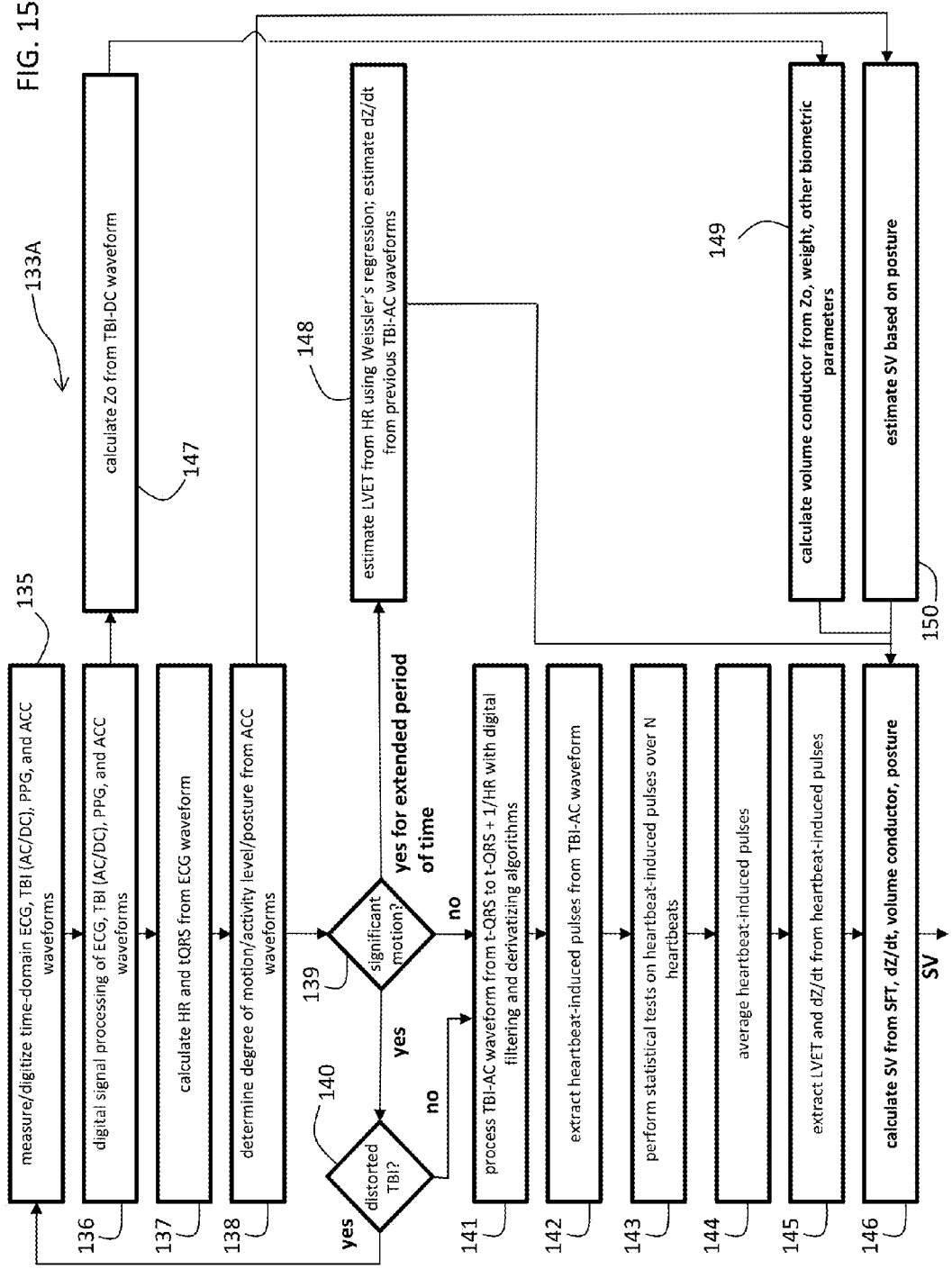

NECKLACE-SHAPED PHYSIOLOGICAL MONITOR

CROSS REFERENCES TO RELATED APPLICATIONS

This application claims the benefit of U.S. Provisional Application No. 61/767,180, filed Feb. 20, 2013, which is hereby incorporated in its entirety including all tables, figures, and claims.

STATEMENT REGARDING FEDERALLY SPONSORED RESEARCH OR DEVELOPMENT

None.

BACKGROUND OF THE INVENTION

1. Field of the Invention

The present invention relates to sensors that measure physiological signals from patients.

2. Description of the Related Art

Medical devices can measure time-dependent electrocardiograms (ECG) and thoracic bioimpedance (TBI) waveforms from patients. Such devices typically connect to disposable electrodes that adhere to the patient's skin and measure bioelectric signals. Analog circuits within the device process the signals to generate the waveform, which with further analysis yields parameters such as heart rate (HR), thoracic fluid levels, stroke volume (SV), 000cardiac output (CO), and respiratory rate (RR). Other systems within the medical devices measure vital signs such as pulse oximetry (SpO2), pulse rate (PR), and temperature (TEMP). Typically the medical device is remote from the patient, and connects to a body-worn sensor through a cable. Adhesive electrodes are sensors that measure ECG and TBI waveform; these are typically worn on the patient's chest or legs. Patients can wear an optical sensor on their fingers or ear to measure photoplethysmogram (PPG) waveforms, which are then processed to yield SpO2 and PR. Temperature is typically measured with a thermometer inserted in the patient's mouth.

Devices that measure ECG and TBI waveforms are often used to characterize patients suffering from congestive heart failure (CHF). CHF occurs when the heart is unable to sufficiently pump and distribute blood to meet the body's needs. The condition is typically preceded by an increase of fluid in the thoracic cavity, and can be characterized by shortness of breath, swelling of the legs and other appendages, and intolerance to exercise. It affects nearly 5.3M Americans and has an accompanying cost of somewhere between $30-50B, with roughly $17B attributed to hospital readmissions. Such events are particularly expensive to hospitals, as readmissions occurring within a 30-day period are not reimbursable by Medicare or private insurance as of October 2012.

In medical centers, CHF is typically detected using Doppler/ultrasound, which measures parameters such as SV, CO, and ejection fraction (EF). Gradual weight gain measured with a simple scale is one method to indicate CHF in the home environment. However, this parameter is typically not sensitive enough to detect the early onset of CHF, a particularly important time when the condition may be ameliorated by a change in medication or diet.

SV is the mathematical difference between left ventricular end-diastolic volume (EDV) and end-systolic volume (ESV), and represents the volume of blood ejected by the left ventricle with each heartbeat; a typical value is about 80 mL. EF relates to EDV and ESV as described below in Eq. 1, with a typical value for healthy individuals being about 50-65%, and an ejection fraction of less than 40% indicating systolic heart failure.

$$EF = \frac{SV}{EDV} = \frac{EDV - ESV}{EDV} \qquad (1)$$

CO is the average, time-dependent volume of blood ejected from the left ventricle into the aorta and, informally, indicates how efficiently a patient's heart pumps blood through their arterial tree; a typical value is about 5 L/min. CO is the product of HR and SV, i.e.:

$$CO = SV \times HR \qquad (2)$$

CHF patients, in particular those suffering from systolic heart failure, may receive implanted devices, such as pacemakers and/or implantable cardioverter-defibrillators, to increase EF and subsequent blood flow throughout the body. These devices also include technologies called 'OptiVol' (from Medtronic) or 'CorVue' (St. Jude) that use circuitry and algorithms within the implanted device to measure the electrical impedance between different leads of the pacemaker. As thoracic fluid increases in the CHF patient, the impedance typically is reduced. Thus this parameter, when read by an interrogating device placed outside the patient's body, can indicate the onset of heart failure.

Corventis Inc. has developed the AVIVO Mobile Patient Management (MPM) System to characterize ambulatory CHF patients. AVIVO is typically used over a 7-day period, during which it provides continual insight into a patient's physiological status by steadily collecting data and wirelessly transmitting it through a small handheld device to a central server for analysis and review. The system consists of three parts: 1) The PiiX sensor, a patient-worn adhesive device that resembles a large (approximately 15" long) bandage and measures fluid status, ECG waveforms, HR, RR, patient activity, and posture; 2) The zLink Mobile Transmitter, a small, handheld device that receives information from the Piix sensor and then transmits data wirelessly to a remote server via cellular technology; and 3) the Corventis Monitoring Center, where data are collected and analyzed. Technicians staff the Monitoring Center, review the incoming data, and in response generate clinical reports made available to prescribing physicians by way of a web-based user interface.

In some cases, physicians can prescribe ambulatory monitors to CHF patients. These systems measure time-dependent ECG waveforms, from which HR and information related to arrhythmias and other cardiac properties are extracted. They characterize ambulatory patients over short periods (e.g. 24-48 hours) using 'holter' monitors, or over longer periods (e.g. 1-3 weeks) using cardiac event monitors. Conventional holter or event monitors typically include a collection of chest-worn ECG electrodes (typically 3 or 5), an ECG circuit that collects analog signals from the ECG electrodes and converts these into multi-lead ECG waveforms; and a processing unit that then analyzes the ECG waveforms to determine cardiac information. Typically the patient wears the entire system on their body. Some modern ECG-monitoring systems include wireless capabilities that transmit ECG waveforms and other numerical data through a cellular interface to an Internet-based system, where they are further analyzed to generate, for example, reports describing the patient's cardiac rhythm. In less sophisticated systems, the ECG monitoring system is worn by the patient, and then returned to a company that downloads all relevant information into a computer, which then analyzes it to generate the report. The report, for example, may be imported into the patient's electronic medical record (EMR). The EMR avails the report to cardiologists or other clinicians, who then use it to help characterize the patient.

SUMMARY OF THE INVENTION

The invention provides a neck-worn sensor (referred to herein as the 'necklace') that is a single, body-worn system that measures the following parameters from an ambulatory patient: HR, PR, SpO2, RR, TEMP, thoracic fluid levels, SV, CO, and a parameter sensitive to blood pressure called pulse transit time (PTT). From SV, a first algorithm employing a linear model can estimate the patient's pulse pressure (PP). And from PP and PTT, a second algorithm, also employing a linear algorithm, can estimate systolic blood pressure (SBP) and diastolic blood pressure (DBP). Thus, the necklace can measure all five vital signs (HR/PR, SpO2, RR, TEMP, and SBP/DPB) along with hemodynamic parameters (SV, CO). It also includes a motion-detecting accelerometer, from which it can determine motion-related parameters such as posture, degree of motion, activity level, respiratory-induced heaving of the chest, and falls. The necklace can operate additional algorithms to process the motion-related parameters to measure vital signs and hemodynamic parameters when motion is minimized and below a pre-determined threshold, thereby reducing artifacts. Moreover, it estimates motion-related parameters such as posture to improve the accuracy of calculations for vital signs and hemodynamic parameters.

The necklace measures all of the above-mentioned properties while featuring a comfortable, easy-to-wear form factor that resembles a piece of conventional jewelry. It is lightweight (about 100 grams) and designed to resemble something other than a conventional medical device. During use, it simply drapes around the neck, and then is held in place by a pair of customized electrodes that measure physiological signals, described in more detail below.

The necklace measures ECG and TBI waveforms using electrical circuitry disposed in the strands that hold it in place. On a bottom surface of the circuit is a customized electrode holder that connects through a magnetic field to a mated set of magnets in a custom electrode. The electrodes contain three separate electrode regions to measure ECG and TBI waveforms. The electrode holders magnetically hold the electrodes in place while providing the necessary electrical couplings. During use, the electrodes are simply held proximal to the electrode holders. Magnetic fields between these components cause the electrodes to easily snap into place. Additionally, the magnets providing the magnetic interface also include a conductive metal coating, meaning they conduct electrical signals sensed by the electrodes into the TBI and ECG analog circuits.

Upper electrodes in each electrode holder supply a drive current for the TBI measurement, while lower electrodes measure a voltage representing the product of the injected drive current and internal impedance in the patient's thoracic cavity. The signals are processed by the TBI analog circuit to generate an analog TBI waveform, which is then sent to an analog-to-digital converter within the left-hand side of the necklace strand for digitization. The middle electrode in each of the three-part electrodes measure signals that pass to an ECG circuit in the right-hand strand, where they are processed with a differential amplifier to generate an analog ECG waveform, which is then sent to the analog-to-digital converter for digitization. Once digitized, both the TBI and ECG waveforms are processed as described below to determine both vital signs and hemodynamic parameters.

Strands disposed on both the left and right-hand sides of the patient's neck feature analog circuitry (right-hand side) and digital circuitry (left-hand side). This circuitry, which is typically disposed on non-flexible fiberglass circuit boards, is connected with flexible circuitry embedded in thin, Kapton films. Typically both the flexible and non-flexible circuits are embedded in a soft, silicone rubber film. Alternating non-flexible and flexible circuitry provides the necklace with all the necessary electronics while allowing it to comfortably bend around the patient's neck.

Other circuitry for temperature, motion, SpO2, wireless data transmission, and data processing are included in strands of the necklace, as is described in more detail below.

The necklace's form factor is designed for comfort and ease of use, with the ultimate goal of improving patient compliance so that the above-mentioned parameters can be measured in a continuous manner and on a day-to-day basis. The system is targeted for elderly, at-home patients, e.g. those suffering from chronic conditions such as CHF, diabetes, and chronic obstructive pulmonary disease (COPD). It is worn around the patient's neck, a location that is unobtrusive, comfortable, removed from the hands, and able to bear the weight of the sensor without being noticeable to the patient. The neck and thoracic cavity are also relatively free of motion compared to appendages such as the hands and fingers, and thus a sensor affixed to this location minimizes motion-related artifacts. Moreover, as described above, such artifacts are compensated for, to some degree, by the accelerometer within the necklace.

The necklace also features other components that simplify it and improve ease of use. For example, it includes a Bluetooth transmitter that sends data (e.g. waveforms and numerical values) to the patient's existing cellular telephone; from there, the data can be forwarded to a physician for further review. The electrodes and associated electrode holders include mated magnets so that, prior to a measurement, the electrodes simply 'snap' into place, thus eliminating the need for cumbersome snaps and rivets that can be difficult for elderly patients to connect. A battery housed in a bottom portion of the necklace (i.e., where an amulet would connect to a conventional necklace) can be easily replaced without removing the necklace's strands, which attach to the patient with the magnetically connected electrodes. In this manner, a fresh battery can be installed when the original battery begins to run low on power, thus allowing the necklace to be used continuously for extended periods of time (e.g. for patient monitoring in a hospital or nursing home).

SpO2 is the one vital sign that is not measured directly from the neck. Here, a circuit board for processing PPG waveforms used to calculate SpO2 and PR resides in the necklace. During a measurement, an optical sensor, which includes separate light-emitting diodes operating in the red (e.g. 600 nm) and infrared (e.g. 800 nm) spectral regions, connects through a flexible cable to the circuit board. The optical sensor simply clips to the base of the ear, where it measures PPG waveforms with both red and infrared wavelengths. An algorithm operating on the microprocessor within the necklace processes these data to determine SpO2, as is described in more detail below. Additionally, PR can be calculated from neighboring pulses in the PPG waveform.

PTT, as described above, correlates inversely with both SBP and DPB. It is calculated from a time difference between the maximum of the ECG waveform (called the QRS complex), and a fiducial point on the TBI waveform (e.g. the onset of the waveform, or the point of maximum slope, as determined from the maximum of the mathematical derivative). Alternatively, PTT can be measured from the ECG QRS and a similar fiducial point on the PPG waveform measured from the ear. Once determined, the inverse of PTT can be used with a calibration measurement (e.g. one performed with a conventional cuff-based blood pressure monitor) to estimate SBP/DBP. Alternatively, the un-calibrated value of PTT can be used to estimate trends in SBP and DPB.

It is well know that PP correlates with SV, and typically this correlation is defined by a single, linear relationship that extends across all patients. Additionally, changes in SV correlate extremely well with changes in PP. Thus, TBI-determined SV yields an independent measurement of PP, and this in turn can increase the accuracy of SDP and DBP.

In one aspect, the invention provides a system for measuring PTT that is worn around a patient's neck. The system features an ECG system with an analog ECG circuit in electrical contact with at least two ECG electrodes that measure an analog ECG waveform. Also included in the necklace is an impedance system with an analog impedance circuit in electrical contact with at least two impedance electrodes that measure an analog impedance waveform. A digital processing system, featuring a microprocessor and analog-to-digital converter, receive the analog ECG and impedance waveforms, and then digitize them to form corresponding digital waveforms. A cable, worn around the patient's neck, houses both the analog ECG and impedance circuits, and the digital processing system. An algorithm running on the microprocessor processes the digital ECG waveform to determine a first time point, and the digital impedance waveform to determine a second time point. It then analyzes the first and second time points to determine PTT.

In embodiments, the cable that houses the above-mentioned circuit elements typically includes a collection of wires that connect the ECG and impedance systems to the digital processing system. Such a system minimizes cable clutter around the patient's neck, as the components that make up the necklace are also carefully designed electrical conductors. The wires can be embedded in a flexible circuit or conductor. Within the necklace, these flexible elements typically alternate with non-flexible circuit boards that support the ECG, impedance, and digital processing systems.

In embodiments, the cable draped around the patient's neck includes a first ECG electrode in a first segment that contacts a first side of the patient's chest, and a second ECG electrode in a second segment that contacts a second, opposing side of the patient's chest. The first and second segments can also include, respectively, first and second impedance electrodes that contact the chest just below the ECG electrodes.

In typical embodiments, the impedance system includes four distinct electrodes: a first and current-injecting electrode, and a first and second voltage-measuring electrode. Typically both the first and second segments include the current-injecting and voltage-measuring electrodes, along with an ECG electrode, as described above.

In embodiments, the necklace includes a battery system that powers the ECG, impedance, and digital processing system. Like these systems, the battery is within the necklace's cable, and is typically located between the first and second segments, where it resembles an amulet. The battery system features a connector that is mated to a similar connector in the necklace so that the battery system can be detached, removed, and replaced with another battery.

In other embodiments, the necklace includes a wireless transceiver within the cable. Typically this system operates on a protocol such as Bluetooth or 802.11a/b/g/n. It can also include a USB connector in electrical contact with a flash memory system.

In another aspect, the invention provides a method for measuring PTT. Such a method is typically accomplished with computer code programmed into the microprocessor that runs an algorithm. The algorithm determines a first time point from the digital ECG waveform, and a second time point from the digital impedance waveform. It then calculates PTT from the difference between the first and second time points.

In embodiments, the algorithm involves taking a mathematical first derivative of the digital impedance waveform, and then processing the mathematical first derivative to determine the second time point. For example, the algorithm can detect a maximum value of the mathematical first derivative, which is a point representing the maximum flow rate of blood through the aorta, and use this for the second time point. The algorithm can also use other fiducial points from the mathematical derivative for the second time point, e.g. an inflection point or zero point crossing. For the first time point, the algorithm typically uses the ECG QRS complex, which can be easily detected from the digital ECG waveform using a beat-picking algorithm.

Once PTT is determined, the algorithm can use it to estimate a blood pressure value. Without using a calibration of some sort, PTT can yield trends in both SBP and DPB. In other embodiments, the algorithm collectively processes PTT with a calibration value to determine an absolute blood pressure value. For example, the necklace can receive the calibration value with the internal wireless transceiver, and then use this to calculate the absolute blood pressure value.

In a related aspect, the invention provides a method to determine PTT and then blood pressure using a PPG waveform measured with a pulse oximetry circuit within the necklace. Typically the pulse oximetry circuit connects through a cable to an optical sensor that connects to one of the patient's ears. Collectively, these components form a pulse oximetry system. The optical sensor features a first light source operating in the red spectral region, and a second light source operating in the infrared spectral region. During a measurement, both light sources generate radiation that passes through a portion of the patient's ear (e.g. the earlobe), where it is detected with a light-sensitive diode (e.g. a photodiode) to generate PPG waveforms. An algorithm processes digital versions of waveforms generated with red and infrared radiation to calculate a value of SpO2.

In another aspect, the invention provides a system that measures PTT during periods of motion. Here, the necklace includes a motion sensor (e.g. an accelerometer) within the cable. It measures a motion signal from the patient. Using algorithms similar to those described above, the microprocessor within the necklace determines a PTT value from the ECG and impedance (or PPG) waveforms when the motion signal, or a processed version thereof, is below a pre-determined threshold value. This value indicates a degree of motion that may corrupt waveforms measured by the impedance or pulse oximetry systems, as these waveforms are particularly sensitive to motion.

In yet another aspect, the necklace measures RR, and it includes a motion sensor that measures a motion signal which the necklace processes in a manner similar to that described above. In this way, RR measurements are made without containing motion-related artifacts. The necklace measures RR from the impedance waveform, e.g. by taking a mathematical first derivative of the waveform and then counting fiducial points (e.g. maximum values, inflection points, or zero point crossings) to determine RR. In other embodiments, an algorithm calculates a frequency-domain transform (e.g. a Fourier Transform) of the digital impedance waveform, and then processes a peak in the transform to determine RR. In embodiments, the algorithm can also analyze respiratory-induced motion components in the motion signal, and analyze these along with components in the impedance waveform to determine RR. For example, the algorithm can deploy an adaptive filter, wherein optical filter parameters are determined from a first waveform (e.g. the motion signal), and then applied to a second waveform (e.g. the impedance waveform).

The invention has many advantages. In general, it combines a comfortable sensor system that resembles a conventional piece of jewelry, but includes all the measurement electronics of a sophisticated physiological monitor. This system, referred to herein as the 'necklace', is comfortable and easy to wear, thus improving patient compliance. It integrates with a web-based software system that allows a clinician to monitor a robust set of physiological parameters from a patient, e.g. one suffering from CHF. The patient can be located at home, or in the hospital.

BRIEF DESCRIPTION OF THE DRAWINGS

FIG. 13 shows screen captures from a software application operating on the cellular telephone of FIG. 12;

FIG. 15 shows a flow chart of an algorithm used to calculate SV and other physiological parameters during periods of motion.

DETAILED DESCRIPTION OF THE INVENTION

As described above, the necklace according to the invention provides a simple, easy-to-wear sensor that measures all vital signs (HR/PR, SpO2, RR, TEMP, and SBP/DBP), hemodynamic parameters (thoracic fluid levels, CO, SV), and motion-related parameters (posture, degree of motion, activity level, and falls). Perhaps the most complex measurement made by the necklace is that for blood pressure, i.e. SBP and DBP. These parameters are determined from PTT separating heartbeat-induced pulses in the ECG and TBI waveforms, coupled with a PP determined from SV determined from the TBI waveform. Using these measurement systems, the necklace's measurement of SBP and DBP is both continuous and cuffless.

Also innovative is the necklace's measurement of SpO2. Here, an optical sensor featuring red and infrared light-emitting diodes (LEDs) clips on to the patient's ear to measure PPG waveforms. These signals pass through a flexible cable to circuitry within the necklace that processes them to determine SpO2.

All analog and digital electronics associated with these measurements are integrated into the strands of the necklace. This means a single component, shaped like a piece of conventional jewelry as opposed to a bulky medical device, measures a robust set of parameters that can characterize a patient using both one-time and continuous measurements. Measurements can take place over just a few minutes or several hours, and are made in medical facilities and at home. The necklace includes a simple LED in its amulet to indicate high-level conditions (e.g., red/yellow/green illuminations depending on the patient's health, as determined from the vital signs and hemodynamic parameters). Also in the amulet is a battery that is easily replaced for long-term, continuous measurements. The necklace includes a wireless transmitter (operating Bluetooth and/or 802.11a/b/g/n) that sends data to, e.g., a conventional mobile device (e.g. cellular telephone, tablet computer, desktop/laptop computer, or plug-in hub).

Figure 1:
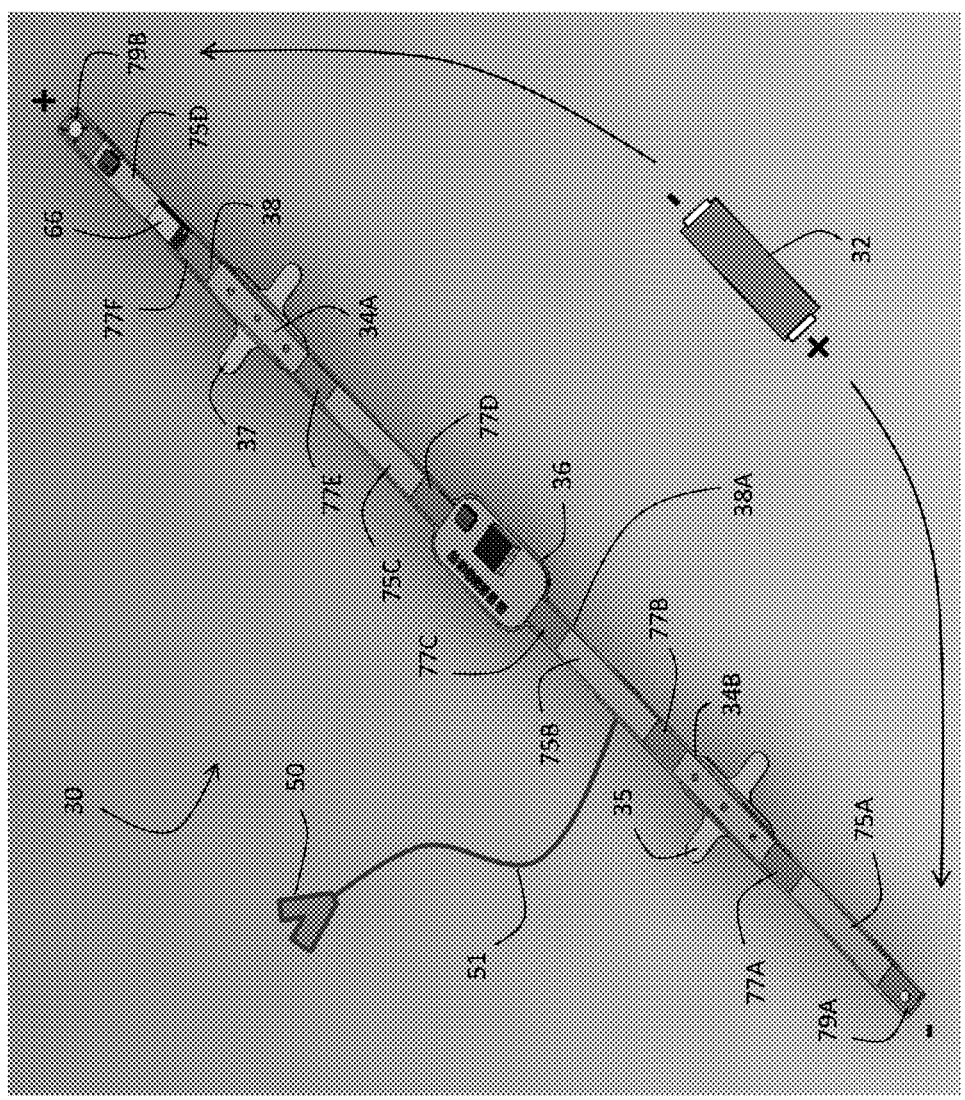
FIG. 1 shows a three-dimensional image of the necklace according to the invention that measures vital signs, hemodynamic parameters, and motion/posture/activity level from an ambulatory patient.

More specifically, FIG. 1 shows the necklace 30 that, during use, is comfortably worn around the patient's neck like a conventional necklace. In this design, the necklace's cable includes all circuit elements, which are typically distributed on an alternating combination of rigid, fiberglass circuit boards and flexible Kapton circuit boards. Typically these circuit boards are potted with a protective material, such as silicone rubber, to increase patient comfort and protect the underlying electronics. The battery for this design can be integrated directly into the cable, or connect to the cable with a conventional connector, such as a stereo-jack connector, micro-USB connector, or magnetic interface.

The necklace 30 is designed for patients suffering from CHF and other cardiac diseases, such as cardiac arrhythmias, as well as patients with implanted devices such as pacemakers and ICDs. Using the magnetically connected electrodes described in more detail below, it makes impedance measurements to determine CO, SV, and fluid levels, and ECG measurements to determine a time-dependent ECG waveform and HR. Additionally it measures RR, TEMP, SpO2, PR, location, and motion-related properties such as posture, activity level, falls, and degree of motion. The sensor's form factor is designed for both one-time measurements, which take just a few minutes, and continuous measurements, which can take several days. Necklaces are likely familiar to a patient 10 wearing this system, and this in turn may improve their compliance in making measurements as directed by their physician. Ultimately compliance in using the necklace may improve the patient's physiological condition. Moreover, it is designed to make measurements near the center of the chest, which is relatively insensitive to motion compared to distal extremities, like the arms or hands. The necklace's form factor also ensures relatively consistent electrode placement for the impedance and ECG measurements; this is important for one-time measurements made on a daily basis, as it minimizes day-to-day errors associated with electrode placement. Finally, the necklace's form factor distributes electronics around the patient's neck, thereby minimizing bulk and clutter associated with these components and making it more comfortable to the patient.

Figure 9:
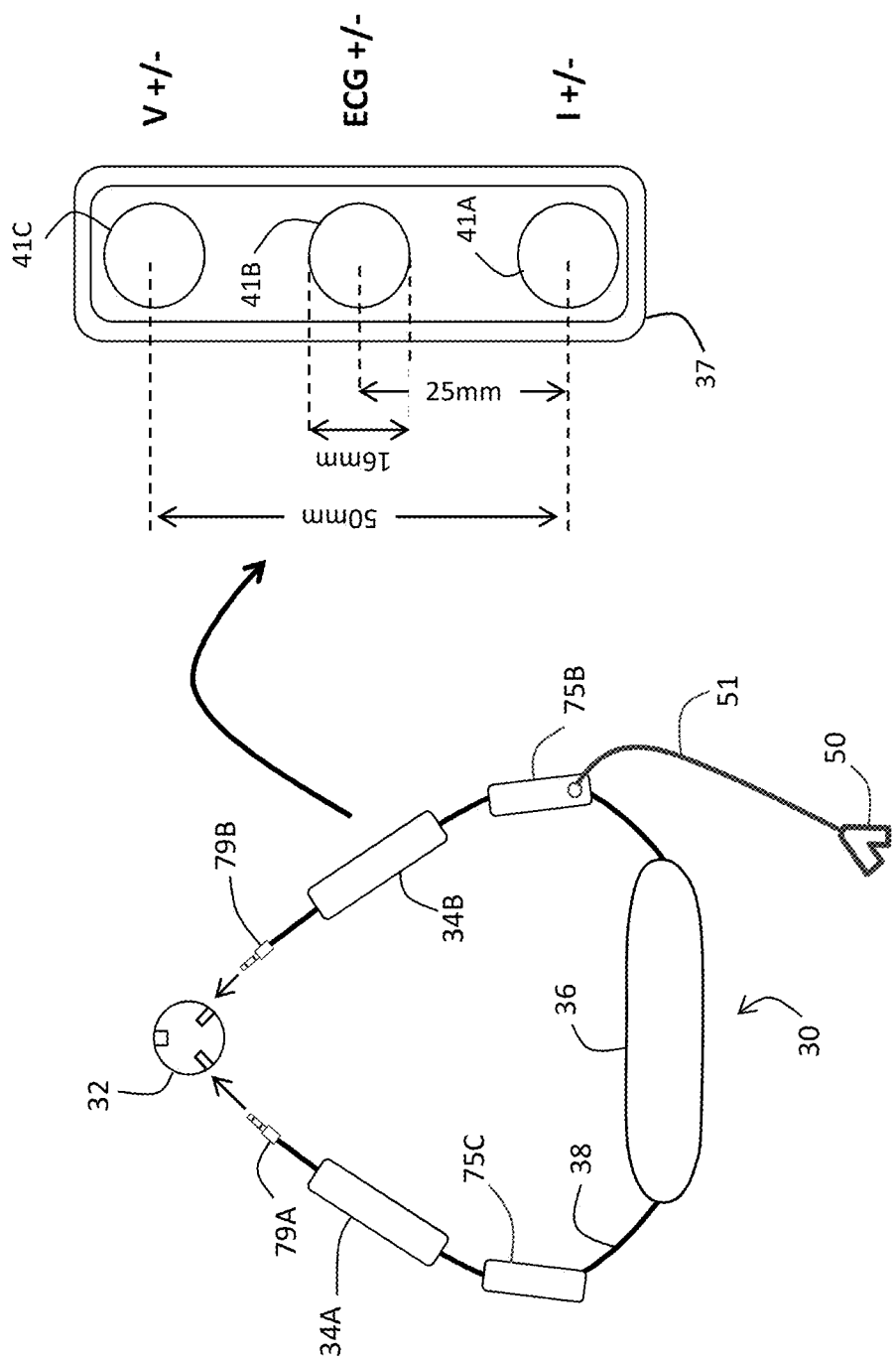
FIG. 9 shows a mechanical drawing of the sensor of FIG. 1 and its associated electrodes for ECG and impedance measurements.

In one embodiment the necklace 30 features a pair of electrode holders 34A, 34B, located on opposing sides, that each include magnets as described in more detail with respect to FIG. 9. The electrode holders 34A, 35A each receive a separate 3-part magnetically connected electrode patch 35, 37. During use, the electrode patches 35, 37 connect to their respective electrode holders 34A, 34B through the magnetic interface, and then stick to the patient's chest when the necklace 30 is draped around their neck. An adhesive backing supports each conductive electrode within the electrode patch 35, 37. The electrodes feature a sticky, conductive gel that contacts the patient's skin. The conductive gel contacts a metal pad that is coated on one side with a thin layer of Ag/AgCl, and connects to a magnet through a via. As described in more detail with respect to FIG. 3, the outer electrodes in each electrode patch are used for the impedance measurement (they conduct signals V+/−, I+/−), while the inner electrodes are used for the ECG measurement (they conduct signals ECG+/−). Proper spacing of the electrodes ensures both impedance and ECG waveforms having high signal-to-noise ratios; this in turn leads to measurements that are relatively easy to analyze, and thus have optimum accuracy. FIG. 9 shows preferred dimensions for these components.

A flexible, flat cable 38 featuring a collection of conductive members transmits signals from the electrode patches 35, 37 to an electronics module 36, which, during use, is preferably worn near the back of the neck. Typically the cable 38 includes alternating regions of rigid fiberglass circuit boards 75A-D and flexible Kapton flex circuits 77A-F to house other electronic components (used, e.g., for other measurement circuits) and conduct electrical signals. The electronic module 36 may snap into a soft covering to increase comfort. The electronics module 36 features a first electrical circuit for making an impedance-based measurement of TBI waveforms that yield CO, SV, RR, and fluid levels, and a second electrical circuit for making differential voltage measurements of ECG waveforms that yield HR and arrhythmia information. The first electrical circuit, which is relatively complex, is shown schematically in FIG. 14; the second electrical circuit is well known in this particular art, and is thus not described in detail here.

Figure 10:
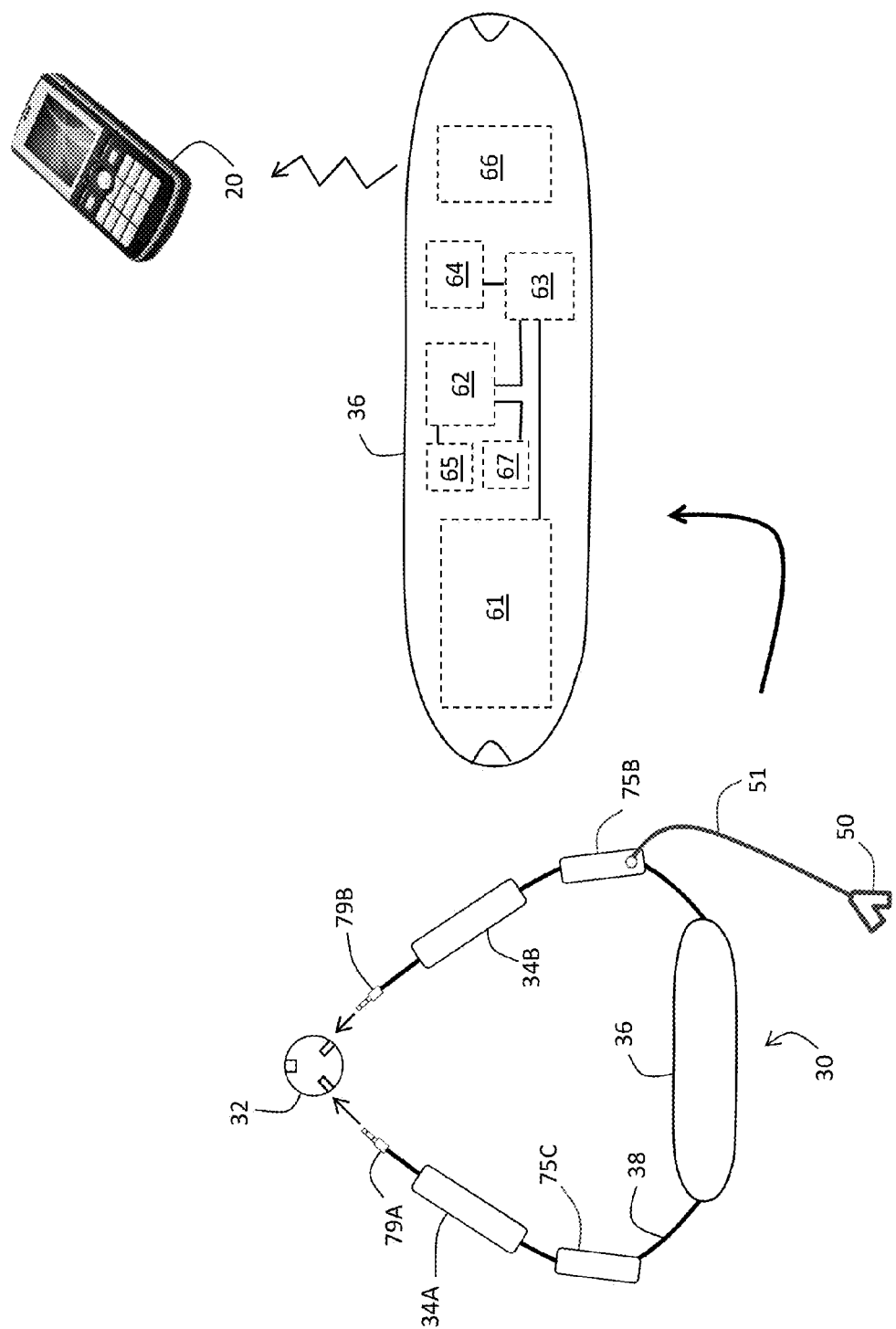
FIG. 10 shows a mechanical drawing of the sensor of FIG. 1 and its associated electronics for ECG, impedance, and digital processing systems.

FIG. 10 shows a more detailed view of the electronics module 36. During a measurement, the second electrical circuit 64 measures an analog ECG waveform that is received by an internal analog-to-digital converter within a microprocessor 62. The microprocessor analyzes this signal to simply determine that the electrode patches are properly adhered to the patient, and that the system is operating satisfactorily. Once this state is achieved, the first 61 and second 64 electrical circuits generate time-dependent analog waveforms that a high-resolution analog-to-digital converter 62 within the electronics module 36 receives and then sequentially digitizes to generate time-dependent digital waveforms. Analog waveforms can be switched over to this component, for example, using a field effect transistor (FET) 63. Typically these waveforms are digitized with 16-bit resolution over a range of about −5V to 5V. The microprocessor 62 receives the digital waveforms and processes them with computational algorithms, written in embedded computer code (such as C or Java), to generate values of CO, SV, fluid level, and HR. An example of an algorithm is described with reference to FIG. 15. Additionally, the electronics module 36 features a 3-axis accelerometer 65 and temperature sensor 67 to measure, respectively, three time-dependent motion waveforms (along x, y, and z-axes) and TEMP values. The microprocessor 62 analyzes the time-dependent motion waveforms to determine motion-related properties such as posture, activity level, falls, and degree of motion. Temperature values indicate the patient's skin temperature, and can be used to estimate their core temperature (a parameter familiar to physicians), as well as ancillary conditions, such as perfusion, ambient temperature, and skin impedance. Motion-related parameters are determined using techniques known in the art. Temperature values are preferably reported in digital form that the microprocessor receives through a standard serial interface, such as I2C, SPI, or UART.

Figure 12:
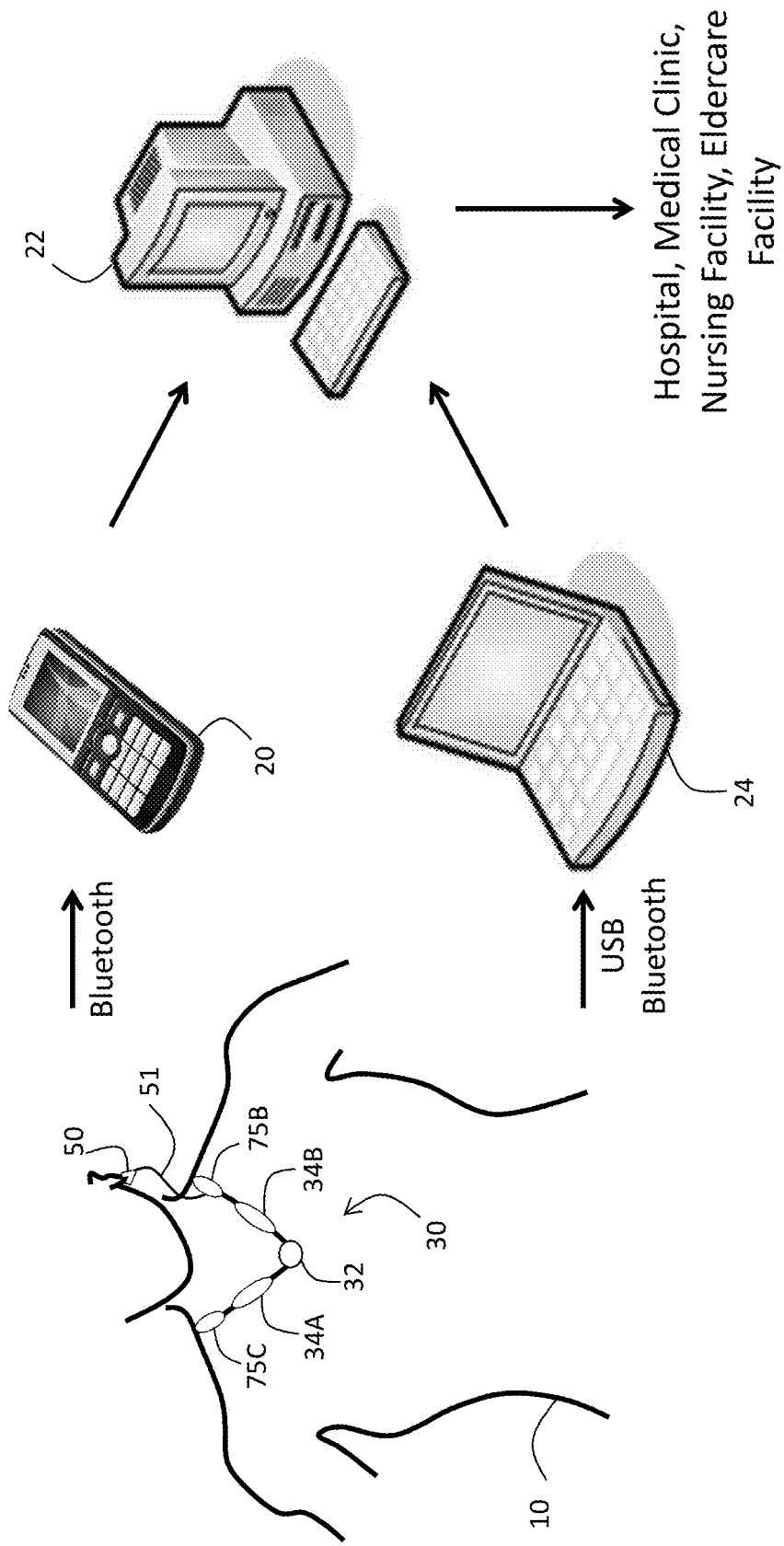
FIG. 12 shows a schematic drawing of the sensor of FIG. 1 transmitting data to a computer server using the patient's cellular telephone and/or personal computer.

Both numerical and waveform data processed with the microprocessor are ported to a wireless transmitter 66, such as a transmitter based on protocols like Bluetooth or 802.11a/b/g/n. From there, the transmitter sends data to an external receiver, such as a conventional cellular telephone, tablet, wireless hub (such as Qualcomm's 2Net system), or personal computer, as is shown in FIG. 12. Devices like these can serve as a 'hub' to forward data to an Internet-connected remote server located, e.g., in a hospital, medical clinic, nursing facility, or eldercare facility.

Figure 11:
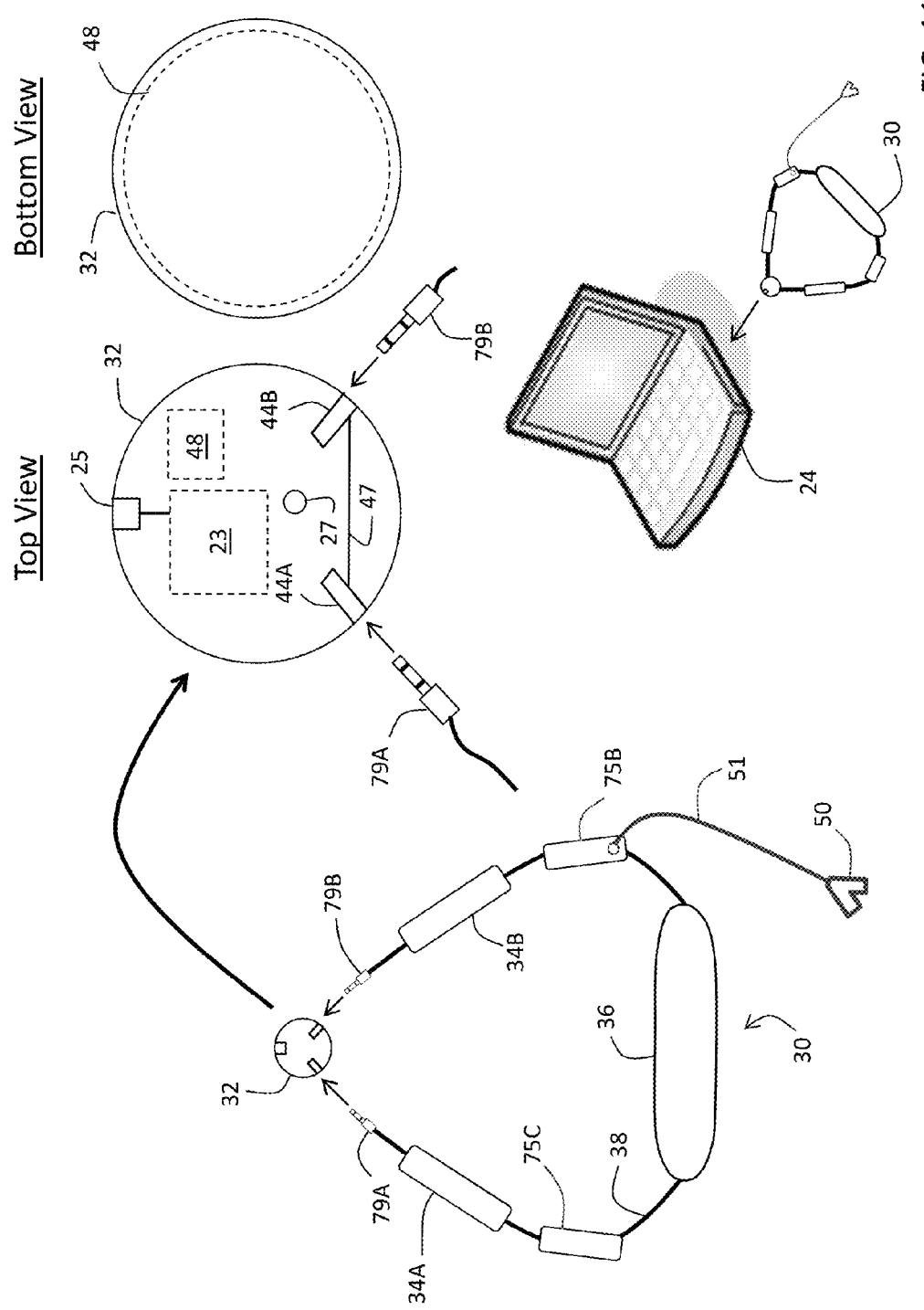
FIG. 11 shows a mechanical drawing of the sensor of FIG. 1 and its associated battery and data-transfer systems.

Referring back to FIG. 1, and in more detail in FIG. 11, a battery module 32 featuring a rechargeable Li:ion battery 48 connects at two points to the cable 38 using a pair of connectors 79A, 79B. During use, the connectors 79A, 79B plug into a pair of mated connectors 44A, 44B that securely hold the terminal ends of the cable 38 so that the necklace 30 can be comfortably and securely draped around the patient's neck. Importantly, when both connectors 79A, 79B are plugged into the battery module 32, the circuit within the necklace 30 is completed, and the battery module 32 supplies power to the electronics module 36 to drive the above-mentioned measurements. The connectors 79A, 79B terminating the cable can also be disconnected from the connectors 44A, 44B on the battery module 32 so that this component can be replaced without removing the necklace 30 from the patient's neck. Replacing the battery module 32 in this manner means the necklace 30 can be worn for extended periods of time without having to remove it from the patient. In general, the connectors 79A, 79B can take a variety of forms: they can be flat, multi-pin connectors, such as those shown in FIG. 1, or stereo-jack type connectors, such as those shown in FIG. 11, that quickly plug into a female adaptor. Both sets of connectors 79A, 79B, 44A, 44B may also include a magnetic coupling so that they easily snap together, thereby making the sensor easy to apply. Typically an LED 27 on the battery module indicates that this is the case, and that the system is operational. When the battery within battery module 32 is nearly drained, the LED 27 indicates this particular state (e.g., by changing color, or blinking periodically). This prompts a user to unplug the battery module 32 from the two connectors, plug it into a recharge circuit (not shown in the figure), and replace it with a fresh battery module as described above. Also contained within the battery module is a flash memory card 23 for storing numerical and waveform data, and a micro-USB port 25 that connects to the flash memory card 23 for transferring data to a remote computer 24. Typically the micro-USB port 25 is also used for recharging the battery when the sensor is removed from the patient. In embodiments, these components can also be moved to the electronics module 36.

As is clear from FIG. 1, the neck-worn cable 38 serves four distinct purposes: 1) it transfers power from the battery module 32 to the electronics module 36; 2) it ports signals from the electrode patches 35, 37 to the impedance and ECG circuits; 3) it ensures consistent electrode placement for the impedance and ECG measurements to reduce measurement errors; and 4) it distributes the various electronics components and thus allows the necklace to be comfortably worn around the patient's neck. Typically each arm of the cable 38 will have six wires: two for the impedance electrodes, one for the ECG electrode, and three to pass signals from the electronics module to electrical components within the battery module. These wires can be included as discrete elements, a flex circuit, or, as described above, a flexible cable.

Non-flexible circuit board 75B includes a standard pulse oximetry circuit, such as the one described in the following patent application, the contents of which are incorporated herein by reference: BODY-WORN PULSE OXIMETER, U.S.S.N. 20100324389, filed Sep. 14, 2009. The circuit drives red and infrared LEDs in an alternating, pulsatile manner, and additionally controls a light-sensitive diode. During a measurement, the light-sensitive diode receives radiation from the LED that either transmits through or reflects off of tissue. Signals from the light-sensitive diode pass through amplifier and filter circuitry to yield PPG waveforms emanating from the red and infrared radiation. These waveforms are then digitized with an analog-to-digital converter, and then processed to extract fiducial points as described in the above-referenced patent application. The fiducial points are then processed with an algorithm that operates Eq. 3, below, to determine a SpO2 value.

$$R = \frac{red(AC)/red(DC)}{infrared(AC)/infrared(DC)} \quad (3)$$

In Eq. 3, the red (AC) and red (DC) represent, respectively, parameters extracted from the AC and DC components of the PPG waveform measured with the red LED. A similar case holds for the infrared (AC) and infrared (DC) values. The term 'AC' signals, as used herein, refers to a portion of a PPG waveform that varies relatively rapidly with time, e.g. the portion of the signal originating by pulsations in the patient's blood. 'DC' signals, in contrast, are portions of the PPG that are relatively invariant with time, e.g. the portion of the signal originating from scattering off of components such as bone, skin, and non-pulsating components of the patient's blood.

More specifically, AC signals are measured from a heartbeat-induced pulse present in both waveforms. The pulse represents a pressure wave, launched by the heart, which propagates through the patient's vasculature and causes a time-dependent increase in volume in both arteries and capillaries. When the pressure pulse reaches vasculature irradiated by the oximeter's optical system, a temporary volumetric increase results in a relatively large optical absorption according to the Beer-Lambert Law. DC signals originate from radiation scattering from static components such as bone, skin, and relatively non-pulsatile components of both arterial and venous blood. Typically only about 0.5-1% of the total signal measured by the photodetector originates from the AC signal, with the remainder originating from the DC signal. Separation of AC and DC signals is typically done with both analog and digital filtering techniques that are well-known in the art.

The R value in Eq. 3, which is sometimes called a 'ratio of ratios' (RoR), represents a ratio of Hb to HbO2. It equates an actual SpO2 value, which ranges from 0-100% O2, to an empirical relationship that resembles a non-linear equation. Above about 70% O2 this equation typically yields values that are accurate to a few percent. Measurements below this value, while not necessarily accurate, still indicate a hypoxic patient in need of medical attention. Additional details for this calculation are described in the above-referenced patent application.

Figure 4:
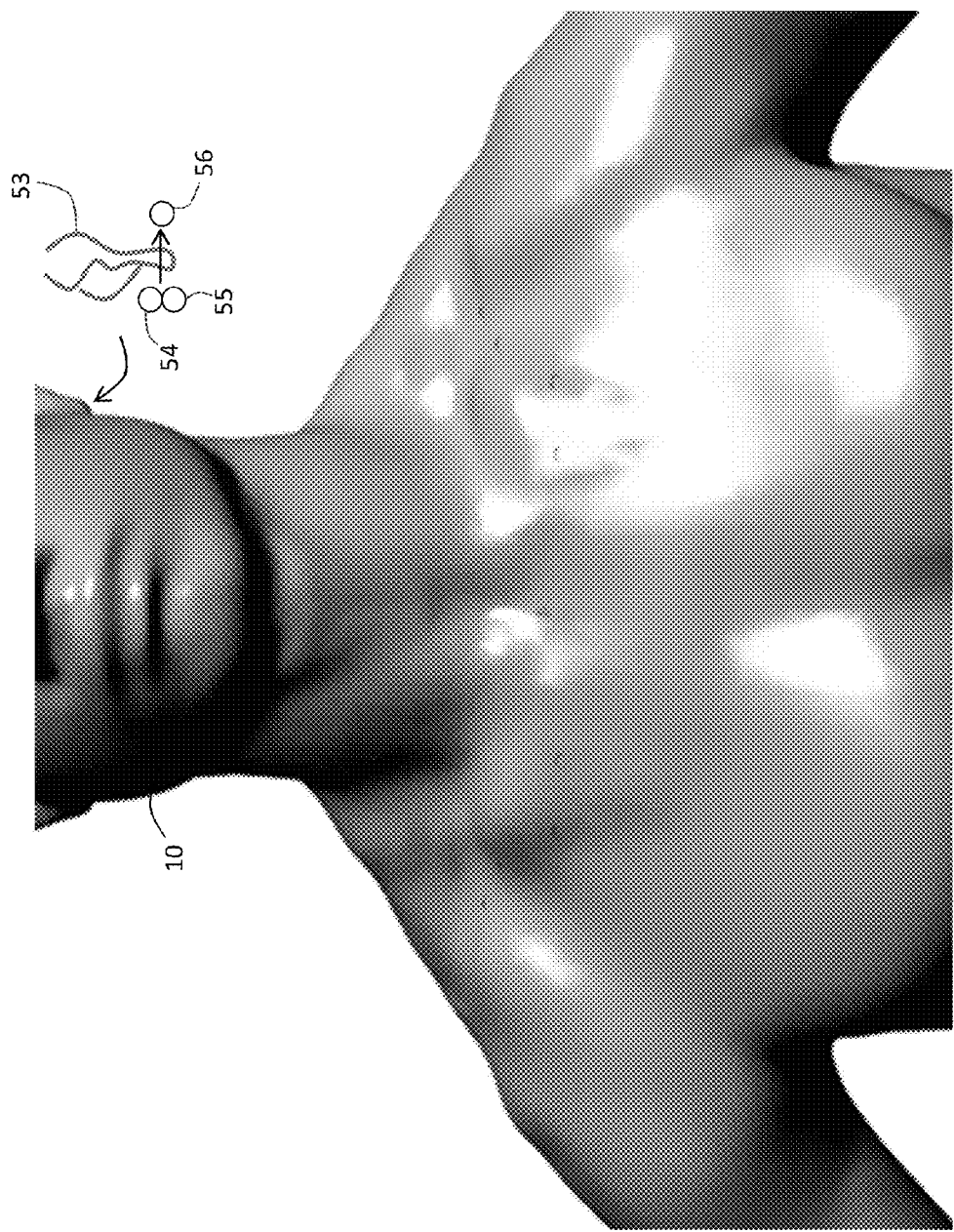
FIG. 4 shows how an optical sensor that connects to the necklace of FIG. 1 measures SpO2 from a patient's earlobe.

As shown in FIG. 1, the pulse oximetry circuit within the circuit board 75B connects through a cable 51 terminated with an optical sensor 50. In typical embodiments, the optical sensor is in the form of a simple clip wherein the red and infrared LEDs are disposed on one arm of the clip, and the light-sensitive diode is disposed on the opposing arm. The clip typically includes a spring-loaded mechanism so that it can easily connect to the patient's ear, as shown in FIG. 4. Most preferably, the optical sensor 50 operates in a transmission mode, meaning the LEDs and light-sensitive diode are positioned as described above. Radiation from the diodes passes through tissue in the earlobe, and then arrives at the light-sensitive diode, where this component and the pulse oximetry circuit process it to form the requisite PPG waveforms needed for Eq. 3. Alternatively, the optical sensor 50 can operate in a transmission mode, meaning the LEDs and light-sensitive diode are disposed on the same side of the sensor 50, and radiation emitted from the LEDs reflects off a surface of the earlobe before arriving at the light-sensitive diode. In this case, the radiation interacts with a thin layer of tissue, where it is modulated accordingly to form the PPG waveforms.

Figure 5:
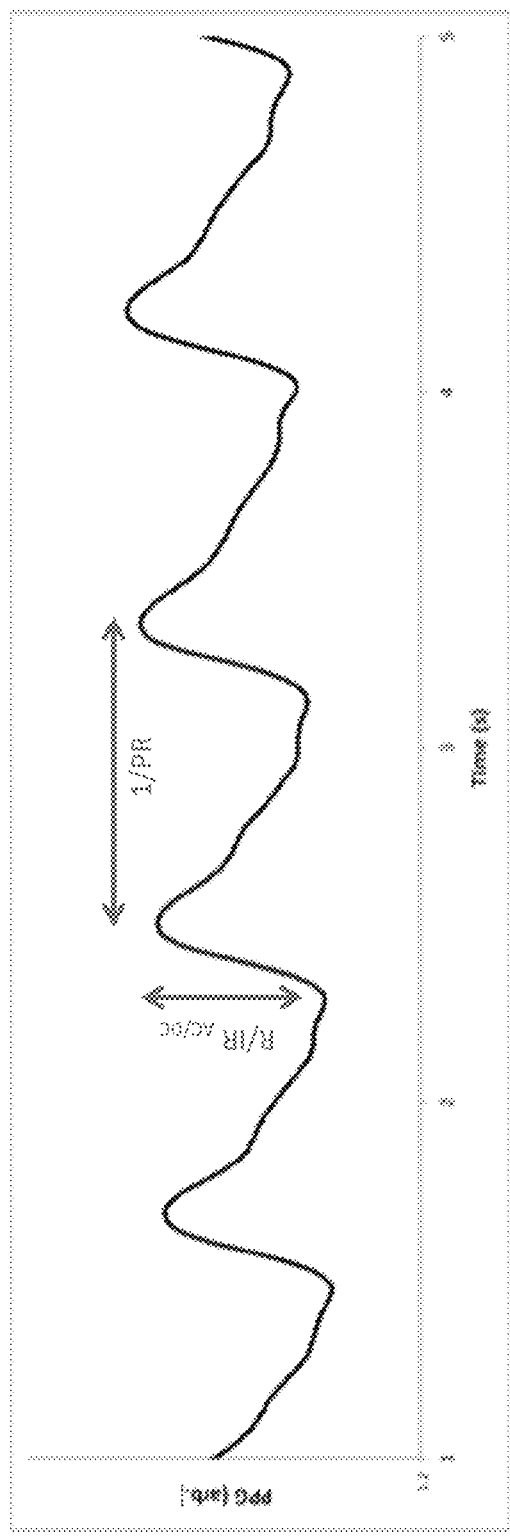
FIG. 5 shows a time-dependent plot of a PPG waveform measured with the optical sensor of FIG. 4.

FIG. 5 shows a conventional PPG waveform measured with the above-described optical sensor. It features a sequence of heartbeat-induced pulses, with the time duration separating the pulses being inversely related to PR. The heartbeat-induced pulses represent blood pulsing in an underlying artery that absorbs (or reflects) incident radiation from the red and infrared LEDs. The PPG waveform also includes a slowly varying baseline that is due to underlying optical absorption by the blood. PPG waveform emanating from both waveforms look similar, with that from infrared radiation typically having a relatively high signal-to-noise ratio.

Figure 2:
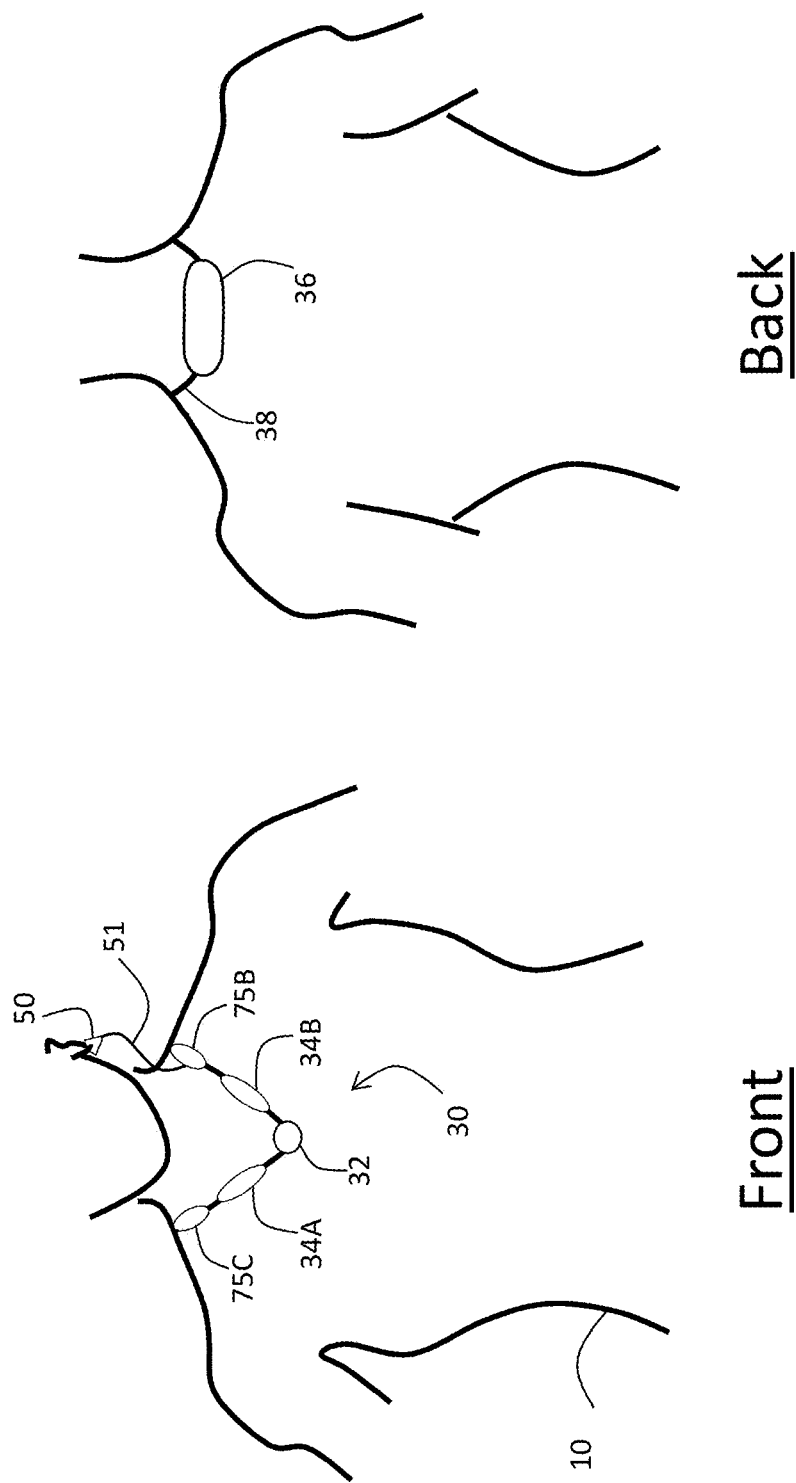
FIG. 2 shows schematic drawings of the front and back of a patient wearing the necklace of FIG. 1.

FIG. 2 shows the above-described necklace 30 worn around the neck of a patient 10. As described above, it includes an electronics module 36 worn on the back of the patient's neck, a battery module 32 in the front, and electrode holders 34A, 34B that connect to the magnetically active electrode patches 35, 37 and secure the cable 38 around the patient's neck that make impedance and ECG measurements.

As shown in the figure, the necklace 30 drapes around the patient's neck so that non-flexible circuit boards 75B, 75C are disposed on opposing sides. Within the circuit board 75B is the above-described pulse oximetry circuit. The cable 51 plugs into a connector on the circuit board 75B so that it can be easily detached. With this configuration, the optical sensor 50 can comfortably connect to the patient's earlobe to measure SpO2 values in an effective manner that minimizes cable clutter, and frees the patient's hands and fingers (where pulse oximetry values are normally made) for other purposes. An added benefit of the configuration shown in FIG. 2 is the reduction of motion artifacts, which can distort PPG waveforms, thus resulting in erroneous SpO2 values. During everyday activities, the head and neck typically move less than the hands and fingers. This means that a sensor configuration like that shown in FIG. 2 is less susceptible to motion-related artifacts than one where the optical sensor is worn on the patient's finger. Ultimately this improves the accuracy of SpO2 values measured from the patient.

Figure 3:
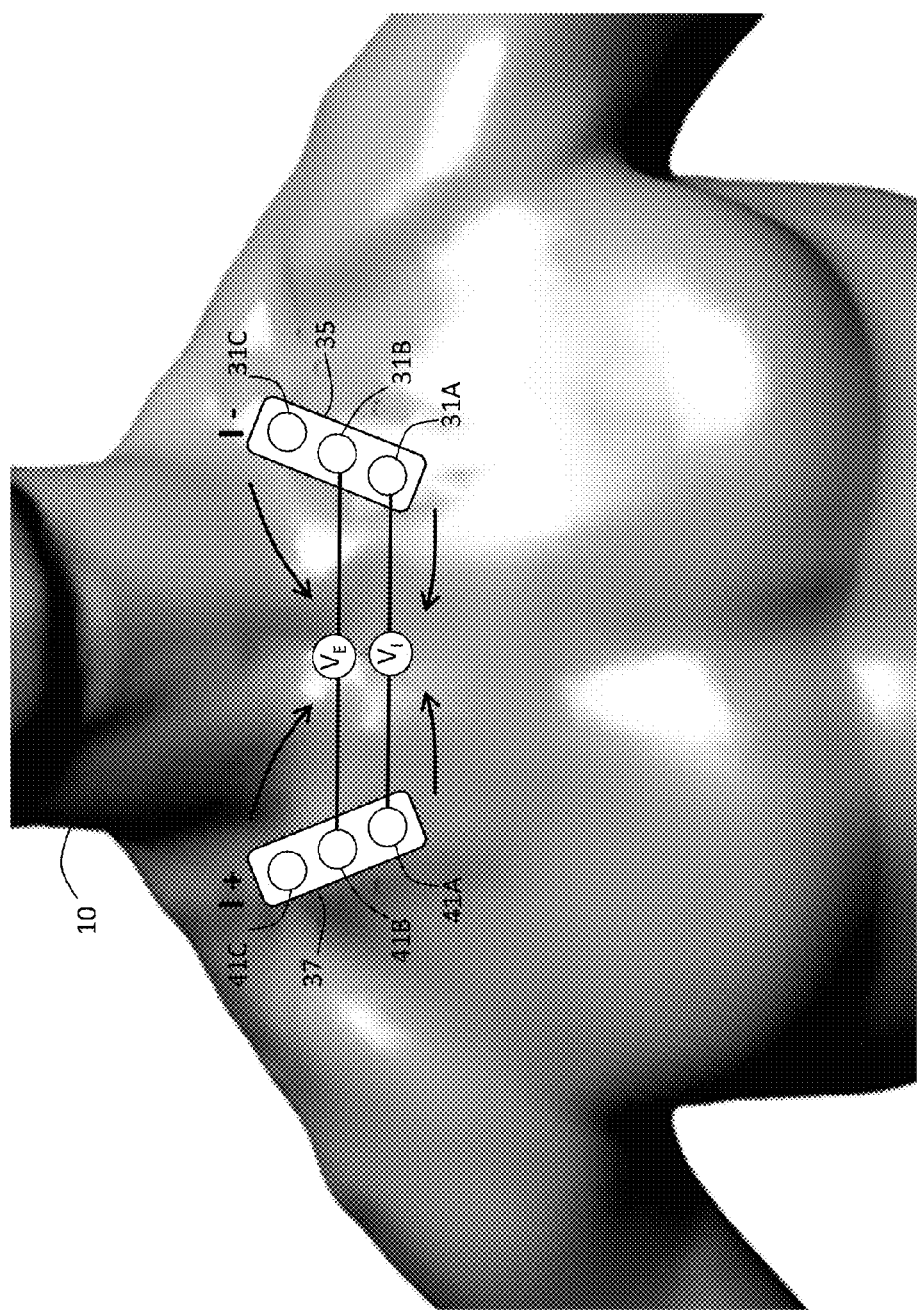
FIG. 3 shows a schematic drawing of electrodes used for the ECG and impedance systems positioned on the patient's chest using the sensor of FIG. 1.

FIG. 3 indicates in more detail how the above-described electrode measures TBI waveforms and CO/SV values from a patient. As described above, 3-part electrode patches 35, 37 within the neck-worn sensor attach to the patient's chest. Ideally, each patch 35, 37 attaches just below the collarbone near the patient's left and right arms. During a measurement, the impedance circuit injects a high-frequency, low-amperage current (I) through outer electrodes 31C, 41C. Typically the modulation frequency is about 70 kHz, and the current is about 4 mA. The current injected by each electrode 31C, 41C is out of phase by 180°. It encounters static (i.e. time-independent) resistance from components such as bone, skin, and other tissue in the patient's chest. Additionally, blood and fluids in the chest conduct the current to some extent. Blood ejected from the left ventricle of the heart into the aorta, along with fluids accumulating in the chest, both provide a dynamic (i.e. time-dependent) resistance. The aorta is the largest artery passing blood out of the heart, and thus it has a dominant impact on the dynamic resistance; other vessels, such as the superior vena cava, will contribute in a minimal way to the dynamic resistance.

Inner electrodes 31A, 41A measure a time-dependent voltage (V) that varies with resistance (R) encountered by the injected current (I). This relationship is based on Ohm's Law, shown below in Eq. 4:

$$V = I \times R \quad (4)$$

During a measurement, the time-dependent voltage is filtered by the impedance circuit, and ultimately measured with an analog-to-digital converter within the electronics module. This voltage is then processed to calculate SV with an equation such as that shown below in Eq. 5, which is the Sramek-Bernstein equation, or a mathematical variation thereof. Historically, parameters extracted from TBI signals are fed into the equation, shown below, which is based on a volumetric expansion model taken from the aortic artery:

$$SV = \delta \frac{L^3}{4.25} \frac{\left(\frac{dZ(t)}{dt}\right)_{max}}{Z_0} LVET \quad (5)$$

In Eq. 5, Z(t) represents the TBI waveform, δ represents compensation for body mass index, Zo is the base impedance, L is estimated from the distance separating the current-injecting and voltage-measuring electrodes on the thoracic cavity, and LVET is the left ventricular ejection time, which is the time separating the opening and closing of the aortic valve, and can be determined from the TBI waveform, or from the HR using an equation called 'Weissler's Regression', shown below in Eq. 6, that estimates LVET from HR:

$$LVET = -0.0017 \times HR + 0.413 \quad (6)$$

Weissler's Regression allows LVET, to be estimated from HR determined from the ECG waveform. This equation and several mathematical derivatives, along with the parameters shown in Eq. 5, are described in detail in the following reference, the contents of which are incorporated herein by reference: '*Impedance Cardiography, Pulsatile blood flow and the biophysical and electrodynamic basis for the stroke volume equations*', Bernstein, *Journal of Electrical Bioimpedance*, Vol. 1, p. 2-17, 2010. Both the Sramek-Bernstein Equation and an earlier derivative of this, called the Kubicek Equation, feature a 'static component', $Z_0$, and a 'dynamic component', ΔZ(t), which relates to LVET and a $(dZ/dt)_{max}/Z_0$ value, calculated from the derivative of the raw TBI signal, Z(t). These equations assume that $(dZ(t)/dt)_{max}/Z_0$ represents a radial velocity (with units of Ω/s) of blood due to volume expansion of the aorta.

In Eq. 5 above, the parameter $Z_0$ will vary with fluid levels. Typically a high resistance (e.g. one above about 30Ω) indicates a dry, dehydrated state. Here, the lack of conducting thoracic fluids increases resistivity in the patient's chest. Conversely, a low resistance (e.g. one below about 19Ω) indicates the patient has more thoracic fluids, and is possibly overhydrated. In this case the abundance of conducting thoracic fluids decreases resistivity in the patient's chest. The TBI circuit and specific electrodes used for a measurement may affect these values. Thus, the values can be more refined by conducting a clinical study with a large number of subjects, preferably those in various states of CHF, and then empirically determining 'high' and 'low' resistance values.

Figure 6:
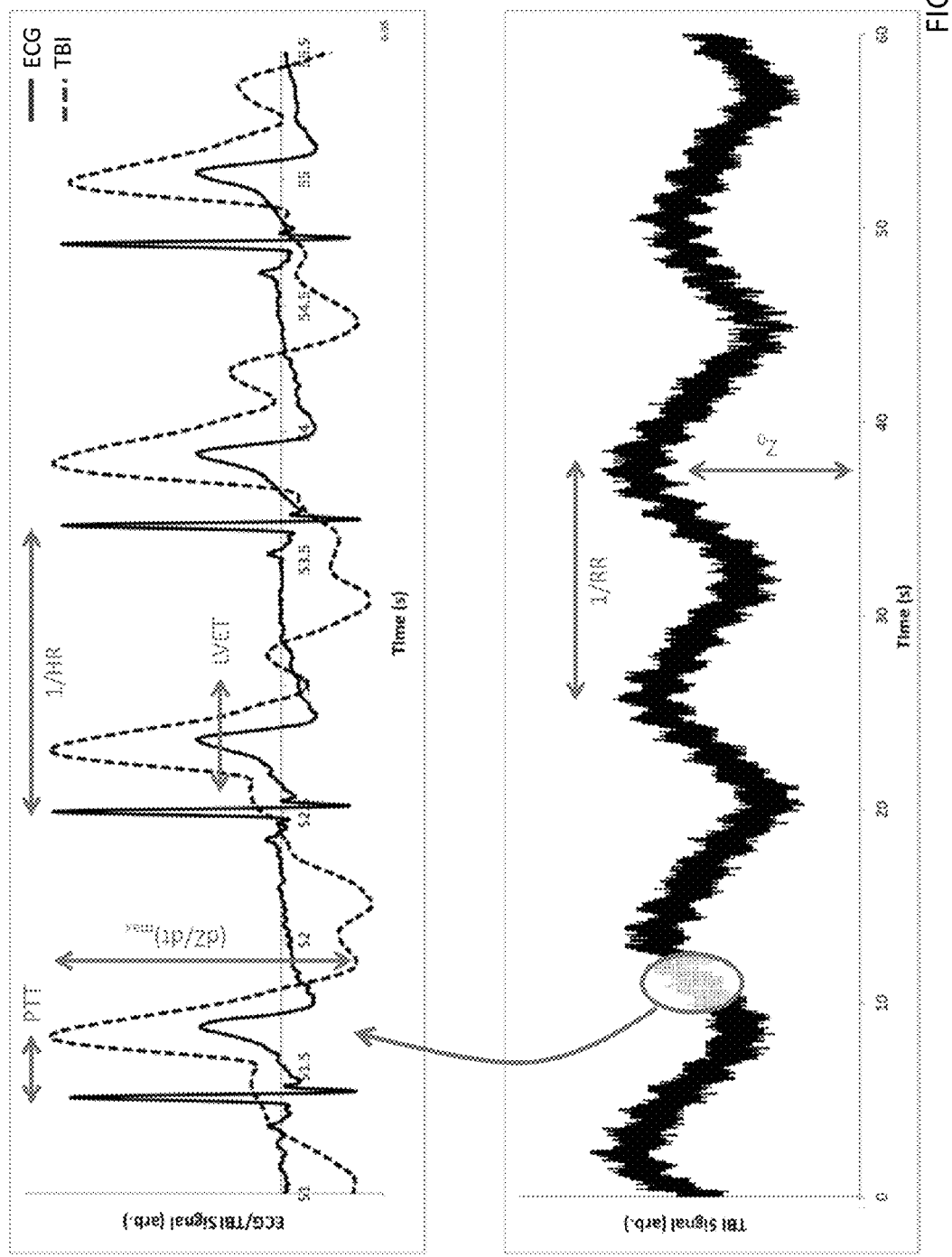
FIG. 6 shows time-dependent plots of ECG and TBI waveforms featuring heartbeat-induced pulses (top) and a TBI waveform showing breathing-induced oscillations, all measured with the necklace of FIG. 1.

FIG. 6 shows derivatized TBI and ECG waveforms measured with the necklace of FIG. 1 plotted over a short (about 5 seconds) time window (top), and TBI waveforms plotted over a longer window (bottom, 60 seconds). Referring first to the top portion of the figure, individual heartbeats produce time-dependent pulses in both the ECG and TBI waveforms. The TBI waveform shown in the figure is the first mathematical derivative of a raw TBI waveform. As is clear from the data, pulses in the ECG waveform precede those in the TBI waveform. The ECG pulses, each featuring a sharp, rapidly rising QRS complex, indicate initial electrical activity in contractions in the patient's heart, and, informally, the beginning of the cardiac cycle. The QRS complex is the peak of the ECG waveform. TBI pulses follow the QRS complex by about 100 ms, and indicate blood flow through arteries in the patient's thoracic cavity. These signals are dominated by contributions from the aorta, which is the largest artery in this region of the body. During a heartbeat, blood flows from the patient's left ventricle into the aorta. The volume of blood is the SV. Blood flow enlarges this vessel, which is typically very flexible, and also temporarily aligns blood cells (called erythrocytes) from their normally random orientation. Both of these mechanisms—enlargement of the aorta and temporary alignment of the erythrocytes—improve electrical conduction near the aorta, thus decreasing the electrical impedance as measured with TBI. The waveform shown in the upper portion of FIG. 4 is a first derivative of the raw TBI waveform, meaning its peak represents the point of maximum impedance change.

A variety of time-dependent parameters can be extracted from the ECG and TBI waveforms. For example, as shown in the upper portion of the figure, it is well known that HR can be determined from the time separating neighboring ECG QRS complexes Likewise, LVET can be measured directly from the TBI pulse. LVET is measured from the onset of the derivatized pulse to the first positive going zero crossing. Also measured from the derivatized TBI pulse is $(dZ/dt)_{max}$, a parameter that is used to calculate SV, as shown in Eq. 5 and described in more detail in the reference described above.

The time difference between the ECG QRS complex and the peak of the derivatized TBI waveform represents a PTT. This value can be calculated from other fiducial points, particularly on the TBI waveform (such as the base or midway point of the heartbeat-induced pulse). But typically the peak of the derivatized waveform is used, as it is relatively easy to develop a software beat-picking algorithm that finds this fiducial point.

PTT correlates inversely to SBP and DBP, as shown below in Eqs. 7-8, where $m_{SBP}$ and $m_{DBP}$ are patient-specific slopes for, respectively, SBP and DBP, and $SBP_{cal}$ and $DBP_{cal}$ are values, respectively, of SBP and DBP measured during a calibration measurement. Without the calibration PTT only indicates relative changes in SBP and DBP. A calibration can be provided with conventional means, such as an oscillometric blood pressure cuff or in-dwelling arterial line. The calibration yields both the patient's immediate value of SBP and DBP. Multiple values of PTT and blood pressure can be collected and analyzed to determine patient-specific slopes $m_{SBP}$ and $m_{DBP}$, which relate changes in PTT with changes in SBP and DBP. The patient-specific slopes can also be determined using pre-determined values from a clinical study, and then combining these measurements with biometric parameters (e.g. age, gender, height, weight) collected during the clinical study.

$$SBP = \frac{m_{SBP}}{PTT} + SBP_{cal} \quad (7)$$

$$DBP = \frac{m_{DBP}}{PTT} + DBP_{cal} \quad (8)$$

In embodiments, waveforms like those shown in the upper portion of FIG. 4 are processed to determine PTT, which is then used to determine either SBP or DBP according to Eqs. 7 or 8. Typically PTT and SBP correlate better than PTT and DBP, and thus this parameter is first determined. Then PP is estimated from SV, calculation of which is described below. Most preferably, instant values of PP and SV are determined, respectively, from the blood pressure calibration and from the TBI waveform.

PP can be estimated from either the absolute value of SV, SV modified by another property (e.g. LVET), or the change in SV. In the first method, a simple linear model is used to process SV (or, alternatively, SV×LVET) and convert it into PP. The model uses the instant values of PP and SV, determined as described above from a calibration measurement, along with a slope that relates PP and SV (or SV×LVET). The slope can be estimated from a universal model that, in turn, is determined using a population study. Alternatively, a slope tailored to the individual patient is used. Such a slope can be selected, for example, using biometric parameters describing the patient, as described above. Here, PP/SV slopes corresponding to such biometric parameters are determined from a large population study, and then stored in computer memory on the necklace. When a necklace is assigned to a patient, their biometric data is entered into the system, e.g. using a mobile telephone that transmits the data to a microprocessor in the necklace via Bluetooth. Then an algorithm on the necklace processes the data and selects a patient-specific slope. Calculation of PP from SV is described in the following reference, the contents of which are incorporated herein by reference: '*Pressure-Flow Studies in Man. An Evaluation of the Duration of the Phases of Systole*', Harley et al., *Journal of Clinical Investigation*, Vol. 48, p. 895-905, 1969. As described in this reference, the relationship between PP and SV for a given patient typically has a correlation coefficient (r) that is greater than 0.9, which indicates excellent agreement between these two properties. Similarly, in the above-mentioned reference, SV is shown to correlate with the product of PP and LVET, with most patients showing an r value of greater than 0.93, and the pooled correlation value (i.e. that for all subjects) being 0.77. This last result indicates that a single linear relationship between PP, SV, and LVET may hold for all patients.

More preferably, PP is determined from SV using relative changes in these values. Typically the relationship between the change in SV and change in PP is relatively constant across all subjects. Thus, similar to the case for PP, SV, and LVET, a single, linear relationship can be used to relate changes in SV and changes in PP. Such a relationship is described in the following reference, the contents of which are incorporated herein by reference: '*Pulse pressure variation and stroke volume variation during increased intra-abdominal pressure: an experimental study*', Didier et al., *Critical Care*, Vol. 15:R33, p. 1-9, 2011. Here, the relationship between PP variation and SV variation for 67 subjects displayed a linear correlation of r=0.93, and extremely high value for pooled results that indicates a single, linear relationship may hold for all patients.

From such a relationship, PP is determined from the TBI-based SV measurement, and SBP is determined from PTT. DBP is then calculated from SBP and PP.

The necklace determines RR from both the TBI waveform, and from a motion waveform generated by the accelerometer (called the ACC waveform), which is typically located in analog circuitry within the necklace, as described above. The bottom portion of FIG. 4 indicates how the TBI waveform yields RR. In this case, the patient's respiratory effort moves air in and out of the lungs, thus changing the impedance in the thoracic cavity. This time-dependent change maps onto the TBI waveform, typically in the form of oscillations or pulses that occur at a much lower frequency than the heartbeat-induced cardiac pulses shown in the upper part of FIG. 4. Simple signal processing (e.g. filtering, beat-picking) of the low-frequency, breathing-induced pulses in the waveform yields RR.

Likewise, the ACC waveform will reflect breathing-induced movements in the patient's chest. This results in pulses within the waveform that have a similar morphology to those shown in the lower portion of FIG. 4 for the TBI waveform. Such pulses can be processed as described above to estimate RR. RR determined from the ACC waveform can be used by itself, or processed collectively with RR determined from the TBI waveform (e.g., using adaptive filtering) to improve accuracy. Such an approach is described in the following patent application, the contents of which are incorporated herein by reference: BODY-WORN MONITOR FOR MEASURING RESPIRATION RATE, U.S.S.N. 20110066062, Filed Sep. 14, 2009.

As shown in the lower portion of FIG. 4, the baseline of the TBI waveform, called Zo, can be easily determined. Zo is used to determine SV, as described above in Eq. 5.

Figure 7:
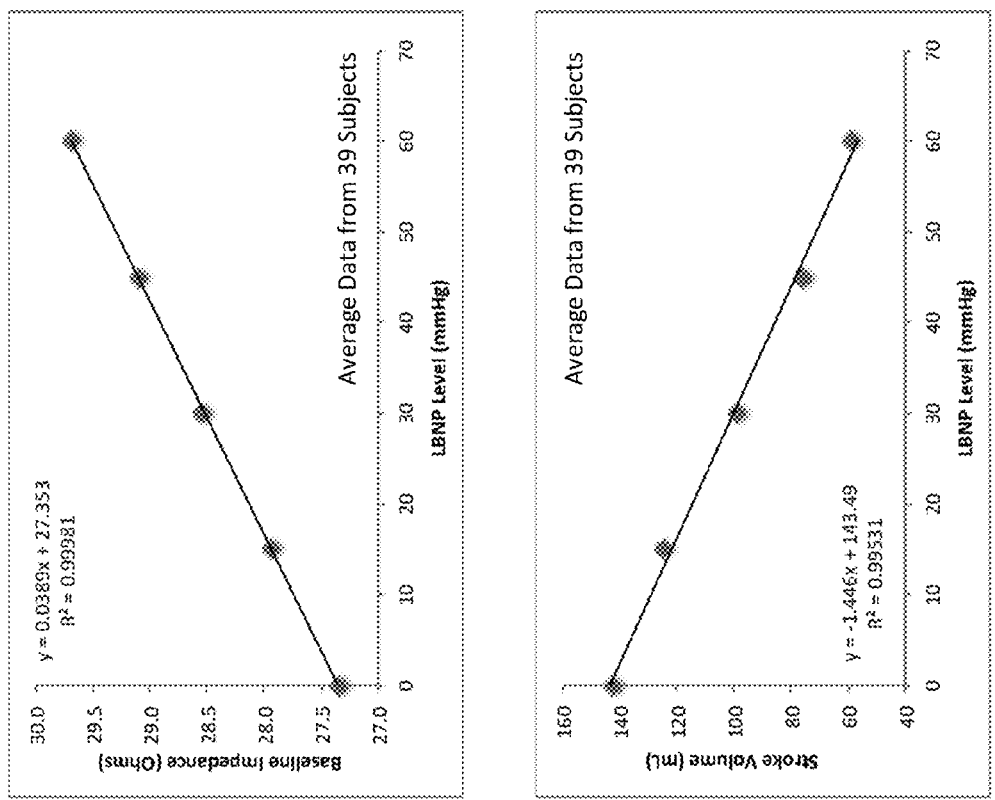
FIG. 7 shows correlation graphs of data, averaged from 39 subjects, of baseline impedance (top) and SV (bottom) compared to lower body negative pressure (LBNP) level, which is an experimental technique for simulating CHF.
Figure 8:
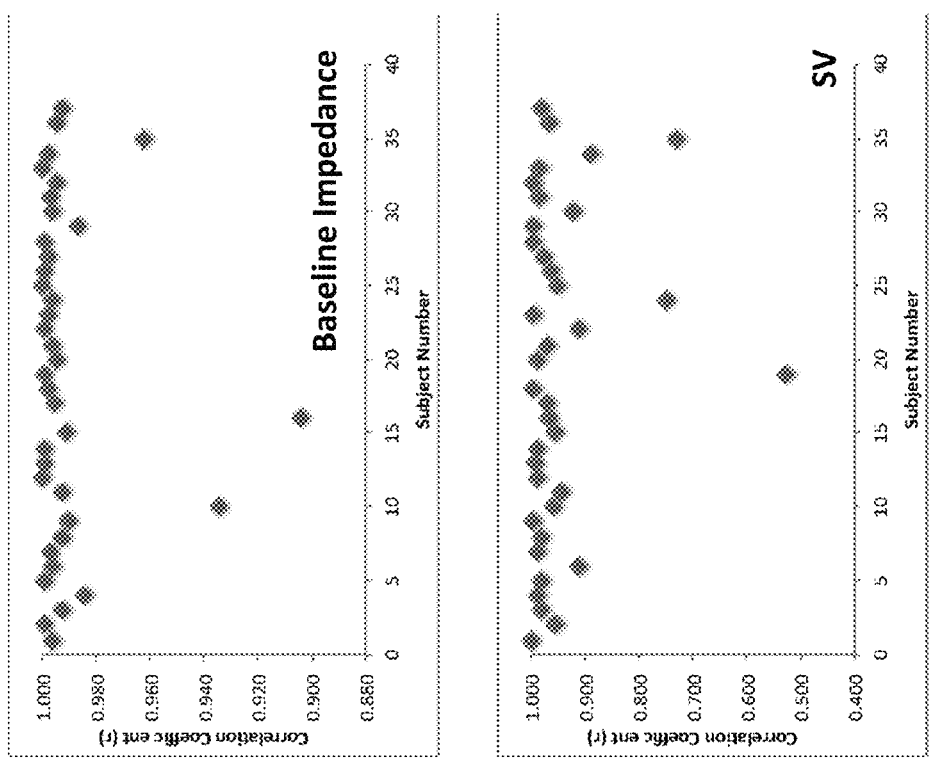
FIG. 8 shows graphs of Pearson's correlation coefficients (r), measured from each of the subjects used to generate the data for FIG. 7, describing the relationship of baseline impedance and SV to LBNP.

FIGS. 7 and 8 show how a process called lower body negative pressure (LBNP) affects baseline impedance Zo and SV. LBNP serves as a surrogate for hemorrhage, a process that typically results in dramatic changes in SV. FIG. 7 shows pooled results from 39 subjects undergoing a gradual increase in LBNP from 0 mmHg (i.e. no change from ambient) to a vacuum of 60 mmHg (corresponding to a loss of blood of about 2 L). The data shown in this figure are averaged over all 39 subjects, and impedance waveforms similar to those described above were measured from the thoracic cavity and analyzed to determine SV and thoracic fluid level. As shown in the top portion of the figure, the change in baseline impedance correlates in a linear manner with the LBNP level, with the agreement between these parameters (Pearson's correlation coefficient $r^2=0.9998$) being extremely high. Here, vacuum applied during LBNP gradually removes conductive fluids from the thoracic cavity, thus decreasing conductivity and increasing baseline impedance. Similarly, the relationship between LBNP level and SV shown in the bottom half of the plot is also linear, with the slope going in the opposite direction as that for the impedance/LBNP correlation. In this case increasing LBNP removes blood from the patient's thoracic cavity, thus reducing their effective blood volume (called 'pre-load') and essentially simulating hemorrhage. During hemorrhage, the body is trained to reduce blood flow by decreasing the amount of blood pumped by the heart (the SV) to preserve perfusion of the internal organs. Thus, it is expected that increasing LBNP will systematically decrease SV, which is exactly what is shown in the lower half of FIG. 7. The correlation for this relationship is also quite high, with $r^2=0.99531$.

In conclusion, the results shown in FIG. 7 indicate that two parameters that change with the onset of CHF—thoracic fluid level and SV—can be accurately measured with an impedance-based technique, such as that deployed with the sensor described herein.

The data shown in FIG. 7 are averaged over all 39 subjects, while the individual correlation coefficient for each subject for the above-described measurements are shown in FIG. 8. As is clear from these data, 36 out of 39 subjects show a correlation between LBNP level (representing a proxy for fluid level, as described above) and baseline impedance characterized by $r>0.98$, which is extremely high. Similarly, 36 out of 39 subjects show a correlation between LBNP level and SV characterized by $r>0.9$. Both of these plots indicate that the parameters measured by impedance measurements show promise for being an accurate physiological monitor.

FIG. 12 depicts how the necklace 30 shown in FIG. 1 is designed to facilitate remote monitoring of a patient 10. As shown in the top portion of the figure, after the necklace 30 measures the patient, it automatically transmits data through its internal Bluetooth wireless transmitter to the patient's cellular telephone 20. In this case, the cellular telephone 20 preferably runs a downloadable software application that accesses the phone's internal Bluetooth drivers, and includes a simple patient-oriented application that renders data on the phone's screen. From there, using its internal modem, the cellular telephone 20 transmits data to an IP address associated with a computer server 22. The computer server 22, in turn, renders a web-based system that displays data for clinicians at a hospital, medical clinic, nursing facility, or eldercare facility. The web-based system may show ECG and TBI waveforms, trended numerical data, the patient's medical history, along with their demographic information. A clinician viewing the web-based system may, for example, analyze the data and then call the patient 10 and have them adjust their medications or diet. Alternatively, as shown in the lower half of the figure, the necklace 30 can automatically transmit data through Bluetooth to a personal computer 24, which then uses a wired or wireless Internet connection to transmit data to the computer server 22. Here, the personal computer 24 runs a custom software program to download data from the sensor 22, display it for the patient in an easy-to-understand format, and then forward it to the computer server for a relatively complex analysis as described above. In yet another embodiment, the necklace 30 is directly plugged into the personal computer 24 through a USB connection, and data are downloaded using a wired connection and forwarded to the computer server 22 as described above.

FIG. 13 shows examples of user interfaces 90, 91, 92 that integrate with the above-mentioned systems and run on the cellular telephone 20, shown in this case as an iPhone. The user interfaces show information such as patient demographics (interface 90), patient-oriented messages (interface 91), and numerical vital signs and time-dependent waveforms (interface 92). The interfaces shown in the figures are designed for the patient. More screens, of course, can be added, and similar interfaces (preferably with more technical detail) can be designed for the actual clinician. The interfaces can also be used to render operational reports, which are then sent off to a clinician for review.

Figure 14:
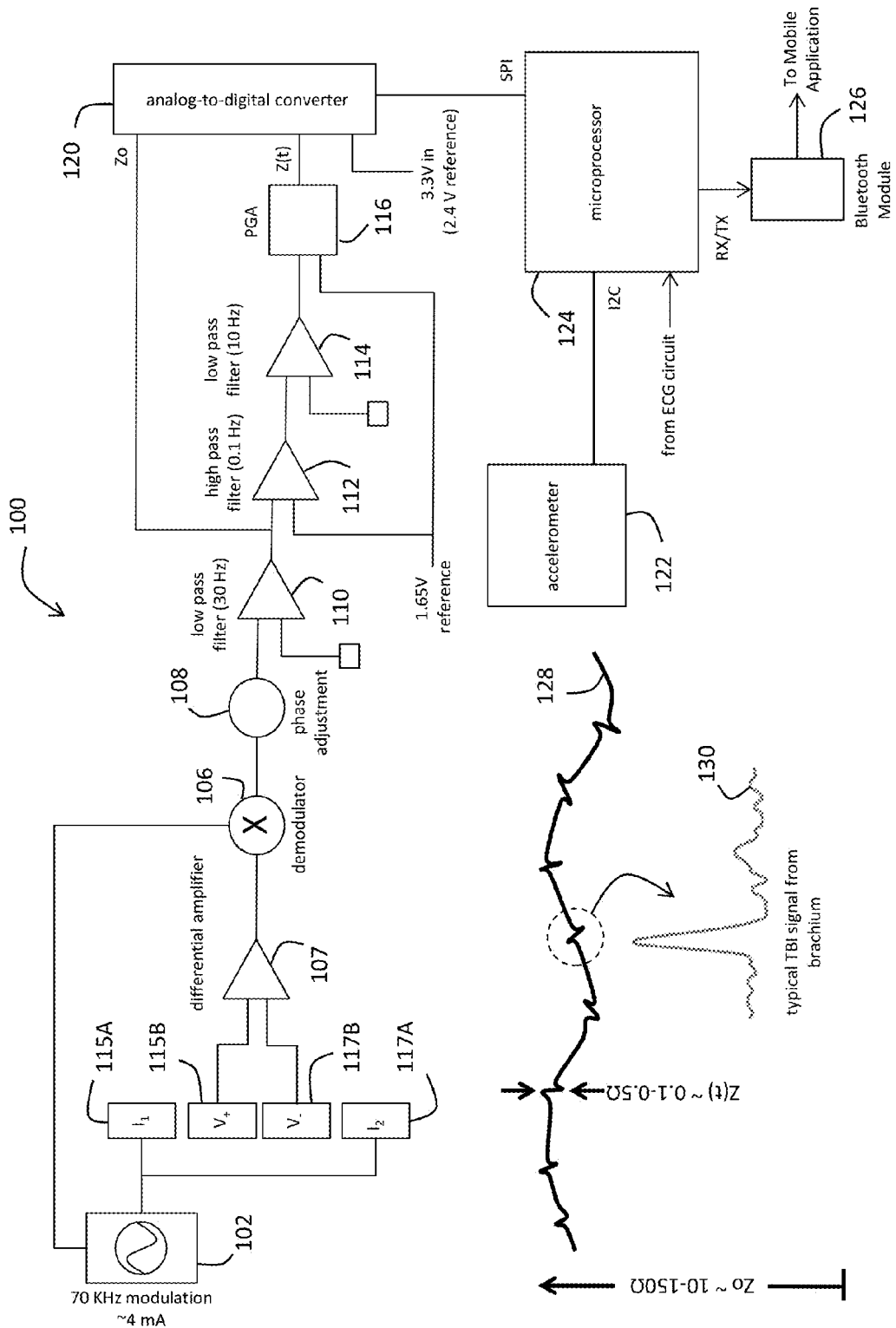
FIG. 14 shows a schematic drawing of an electrical circuit used within the sensor of FIG. 1 to measure the impedance waveform.

FIG. 14 shows an analog circuit 100 that performs the impedance measurement according to the invention. The figure shows just one embodiment of the circuit 100; similar electrical results can be achieved using a design and collection of electrical components that differ from those shown in the figure.

The circuit 100 features a first magnetically connected electrode 115A that injects a high-frequency, low-amperage current ($I_1$) into the patient's brachium. This serves as the current source. Typically a current pump 102 provides the modulated current, with the modulation frequency typically being between 50-100 KHz, and the current magnitude being between 0.1 and 10 mA. Preferably the current pump 102 supplies current with a magnitude of 4 mA that is modulated at 70 kHz through the first electrode 115A. A second magnetically connected electrode 117A injects an identical current ($I_2$) that is out of phase from $I_1$ by 180°.

Another pair of magnetically connected electrodes 115B, 117B measure the time-dependent voltage encountered by the propagating current. These electrodes are indicated in the figure as V+ and V−. As described above, using Ohm's law, the measured voltage divided by the magnitude of the injected current yields a time-dependent resistance to ac (i.e. impedance) that relates to blood flow in the aortic artery. As shown by the waveform 128 in the figure, the time-dependent resistance features a slowly varying dc offset, characterized by Zo, that indicates the baseline impedance encountered by the injected current; for TBI this will depend, for example, on the amount of thoracic fluids, along with the fat, bone, muscle, and blood volume in the chest of a given patient. Zo, which typically has a value between about 10 and 150Ω, is also influenced by low-frequency, time-dependent processes such as respiration. Such processes affect the inherent capacitance near the chest region that TBI measures, and are manifested in the waveform by low-frequency undulations, such as those shown in the waveform 128. A relatively small (typically 0.1-0.5Ω) AC component, $\Delta Z(t)$, lies on top of Zo and is attributed to changes in resistance caused by the heartbeat-induced blood that propagates in the brachial artery, as described in detail above. $Z(t)$ is processed with a high-pass filter to form a TBI signal that features a collection of individual pulses 130 that are ultimately processed to determine SV and CO.

Voltage signals measured by the first electrode 115B (V+) and the second electrode 117B (V−) feed into a differential amplifier 107 to form a single, differential voltage signal which is modulated according to the modulation frequency (e.g. 70 kHz) of the current pump 102. From there, the signal flows to a demodulator 106, which also receives a carrier frequency from the current pump 102 to selectively extract signal components that only correspond to the TBI measurement. The collective function of the differential amplifier 107 and demodulator 106 can be accomplished with many different circuits aimed at extracting weak signals, like the TBI signal, from noise. For example, these components can be combined to form a 'lock-in amplifier' that selectively amplifies signal components occurring at a well-defined carrier frequency. Or the signal and carrier frequencies can be deconvoluted in much the same way as that used in conventional AM radio using a circuit that features one or more diodes. The phase of the demodulated signal may also be adjusted with a phase-adjusting component 108 during the amplification process. In one embodiment, the ADS1298 family of chipsets marketed by Texas Instruments may be used for this application. This chipset features fully integrated analog front ends for both ECG and impedance pneumography. The latter measurement is performed with components for digital differential amplification, demodulation, and phase adjustment, such as those used for the TBI measurement, that are integrated directly into the chipset.

Once the TBI signal is extracted, it flows to a series of analog filters 110, 112, 114 within the circuit 100 that remove extraneous noise from the Zo and ΔZ(t) signals. The first low-pass filter 110 (30 Hz) removes any high-frequency noise components (e.g. power line components at 60 Hz) that may corrupt the signal. Part of this signal that passes through this filter 110, which represents Zo, is ported directly to a channel in an analog-to-digital converter 120. The remaining part of the signal feeds into a high-pass filter 112 (0.1 Hz) that passes high-frequency signal components responsible for the shape of individual TBI pulses 130. This signal then passes through a final low-pass filter 114 (10 Hz) to further remove any high-frequency noise. Finally, the filtered signal passes through a programmable gain amplifier (PGA) 116, which, using a 1.65V reference, amplifies the resultant signal with a computer-controlled gain. The amplified signal represents ΔZ(t), and is ported to a separate channel of the analog-to-digital converter 120, where it is digitized alongside of Zo. The analog-to-digital converter and PGA are integrated directly into the ADS1298 chipset described above. The chipset can simultaneously digitize waveforms such as Zo and ΔZ(t) with 24-bit resolution and sampling rates (e.g. 500 Hz) that are suitable for physiological waveforms. Thus, in theory, this one chipset can perform the function of the differential amplifier 107, demodulator 108, PGA 116, and analog-to-digital converter 120. Reliance of just a single chipset to perform these multiple functions ultimately reduces both size and power consumption of the TBI circuit 100.

Digitized Zo and Z(t) waveforms are received by a microprocessor 124 through a conventional digital interface, such as a SPI or I2C interface. Algorithms for converting the waveforms into actual measurements of SV and CO are performed by the microprocessor 124. The microprocessor 124 also receives digital motion-related waveforms from an on-board accelerometer, and processes these to determine parameters such as the degree/magnitude of motion, frequency of motion, posture, and activity level.

FIG. 15 shows a flow chart of an algorithm 133A that functions using compiled computer code that operates, e.g., on the microprocessor 124 shown in FIG. 6. The algorithm 133A is used to measure TBI waveforms in the presence of motion. The compiled computer code is loaded in memory associated with the microprocessor, and is run each time a TBI measurement is converted into a numerical value for CO and SV. The microprocessor typically runs an embedded real-time operating system. The compiled computer code is typically written in a language such as C, C++, Java, or assembly language. Each step 135-150 in the algorithm 133A is typically carried out by a function or calculation included in the compiled computer code.

Algorithms similar to that shown in FIG. 15 can be used to calculate other physiological parameters in the presence of motion, such as SpO2, RR, HR, and PR.

In other embodiments, algorithms can process other waveforms, such as the PPG and ECG waveforms, to extract parameters such as RR. Here, the low-frequency envelope of the waveform indicates RR. In other embodiments, a reflective pulse oximetry system can measure SpO2 without requiring an ear-worn optical sensor, such as that shown in FIG. 4. In this case the sensor uses reflective-mode optical configurations to measure both the red and infrared PPG waveforms. In still other embodiments, the electronics within the necklace, as shown in FIGS. 10 and 11, are moved within the necklace's geometry. For example, they can be moved from the back portion of the necklace to a side portion proximal to the front of the patient's neck.

Still other embodiments are within the scope of the following claims.

What is claimed is:

1. A necklace system for measuring a blood pressure value and configured to be worn around a patient's neck, comprising:
   an electrocardiogram (ECG) system comprising an analog ECG circuit in electrical contact with at least two ECG electrodes, the ECG system configured to generate an analog ECG waveform;
   an impedance system comprising an analog impedance circuit in electrical contact with at least two impedance electrodes, the impedance system configured to generate an analog impedance waveform;
   a wireless system comprising a wireless transceiver configured to receive a blood pressure calibration value;
   a digital processing system comprising a microprocessor and an analog-to-digital converter and configured to receive the analog ECG and impedance waveforms, the analog-to-digital converter configured to digitize the analog ECG waveform to generate a digital ECG waveform and digitize the analog impedance waveform to generate a digital impedance waveform, and the microprocessor configured to process the digital ECG waveform to determine a first time point, process the digital impedance waveform to determine a second time point, and analyze the first and second time points to determine pulse transit time (PTT), and then process the PTT and the blood pressure calibration value to determine the blood pressure value; and,
   a cable configured to be worn around the patient's neck, the cable housing the analog ECG circuit, the analog impedance circuit, the wireless system, and the digital processing system.

2. The necklace system of claim 1, wherein the cable further comprises a plurality of wires that connect the ECG system to the digital processing system, and the impedance system to the digital processing system.

3. The necklace system of claim 1, wherein the cable comprises a flexible circuit that connects the ECG system to the digital processing system.

4. The necklace system of claim 1, wherein the cable comprises a flexible circuit that connects the impedance system to the digital processing system.

5. The necklace system of claim 1, wherein the cable comprises at least two non-flexible circuit boards connected to each other with a flexible conductor.

6. The necklace system of claim 5, wherein the flexible conductor is a flexible circuit.

7. The necklace system of claim 5, wherein the flexible conductor is a plurality of wires.

8. The necklace system of claim 5, wherein one of the non-flexible circuit boards comprises the ECG system, and the other comprises the digital processing system.

9. The necklace system of claim 5, wherein one of the non-flexible circuit boards comprises the impedance system, and the other comprises the digital processing system.

10. The necklace system of claim 1, wherein the cable comprises a first ECG electrode in a first segment configured to contact a first side of the patient's chest, and a second ECG electrode in a second segment configured to contact a second, opposing side of the patient's chest.

11. The necklace system of claim 1, wherein the cable comprises a first impedance electrode in a first segment configured to contact a first side of the patient's chest, and a second impedance electrode in a second segment configured to contact a second, opposing side of the patient's chest.

12. The necklace system of claim 1, wherein the cable comprises a first segment comprising a first ECG electrode and a first impedance electrode, the first segment configured to contact a first portion of the patient's chest, and a second segment comprising a second ECG electrode and a second impedance electrode, the second segment configured to contact a second, opposing segment of the patient's chest.

13. The necklace system of claim 1, wherein the impedance system comprises four distinct electrodes.

14. The necklace system of claim 13, wherein the impedance system comprises a first current-injecting electrode, a second current-injecting electrode, a first voltage-measuring electrode, and a second voltage-measuring electrode.

15. The necklace system of claim 14, wherein the cable comprises a first segment comprising a first ECG electrode, the first current-injecting electrode, and the first voltage-measuring electrode, the first segment configured to contact a first portion of the patient's chest, and a second segment comprising a second ECG electrode, the second current-injecting electrode, and the second voltage-measuring electrode, the second segment configured to contact a second, opposing segment of the patient's chest.

16. The necklace system of claim 1, further comprising a battery system configured to power the ECG system, the impedance system, and the digital processing system.

17. The necklace system of claim 16, wherein the cable comprises the battery system.

18. The necklace system of claim 17, wherein the cable comprises a first connector and the battery system comprises a second connector, with the first connector mated to the second connector so that the battery system can be detachably removed.

19. The necklace system of claim 1, wherein the wireless transceiver is one of a Bluetooth transceiver and an 802.11-based transceiver.

20. The necklace system of claim 1, further comprising a blood pressure system configured to measure the blood pressure calibration value.

21. The necklace system of claim 20, wherein the blood pressure calibration value comprises values for systolic and diastolic blood pressure.

22. The necklace system of claim 20, wherein the blood pressure system comprises a second wireless transceiver configured to pair with the wireless system in the necklace system.

* * * * *